United States Patent [19]
Kleid et al.

[11] Patent Number: 5,888,808
[45] Date of Patent: Mar. 30, 1999

[54] BACTERIAL POLYPEPTIDE EXPRESSION EMPLOYING TRYPTOPHAN PROMOTER-OPERATOR

[75] Inventors: Dennis G. Kleid, San Mateo; Daniel G. Yansura, San Francisco; Herbert L. Heyneker, Burlingame; Giuseppe F. Miozzari, San Carlos, all of Calif.

[73] Assignee: Genentech, Inc., So. San Francisco, Calif.

[21] Appl. No.: 55,960

[22] Filed: Apr. 29, 1993

Related U.S. Application Data

[63] Continuation of Ser. No. 655,215, Feb. 12, 1991, abandoned, which is a continuation of Ser. No. 76,253, Jul. 21, 1987, abandoned, which is a continuation of Ser. No. 685,521, Dec. 24, 1984, abandoned, which is a continuation of Ser. No. 307,473, Oct. 1, 1981, abandoned, which is a continuation of Ser. No. 133,296, Mar. 24, 1980, abandoned.

[51] Int. Cl.[6] .............................. C12N 15/63; C12N 15/70
[52] U.S. Cl. .................. 435/320.1; 435/69.1; 435/69.4; 435/252.33; 435/471; 435/476; 435/488; 536/23.51
[58] Field of Search ............................. 435/6, 69.1, 69.4, 435/71.1, 91, 172.3, 252.3, 320.1; 536/23.51; 935/13, 29, 40, 41, 56, 60, 73

[56] References Cited

U.S. PATENT DOCUMENTS 4,237,224  12/1980  Cohen et al. ..................... 435/91 X
5,145,782   9/1992  Hallewell ......................... 435/320.1

OTHER PUBLICATIONS

Jeffrey H. Miller, Experiments in Molecular Genetics, "Construction of trpR⁻ Derivatives of trp–lac Fusion Strains", pp. 312–315, Cold Spring Harbor Laboratory, 1972.
Miozzari, et al., *J. Bacteriol.*, 133(3): 1457–1466 (1978).
Rodriguez, et al., *Nucleic Acids Research*, 6(10): 3267–3287 (1979).
Goeddel, et al., *Nature*, 281: 544–548 (1979).
Miozzari, et al., *J. Bacteriol.*, 134(1):48–59 (1978).
Goeddel et al, Proc. Natl. Acad. Sci. USA, vol. 76, No. 1, Jan. 1979, "Expression in *Escherichia coli* of Chemically Synthesized Genes for Human Insulin", pp. 106–110.

*Primary Examiner*—Laurie Scheiner
*Attorney, Agent, or Firm*—Walter H. Dreger; Mark T. Kresnak; Flehr Hohbach Test Albritton & Herbert LLP

[57] ABSTRACT

The present invention provides recombinant DNA vehicles which are suitable for the microbial expression of DNA encoding a heterologous polypeptide which comprises a portion of the trp operon having the promoter-operator and leader ribosome binding site, and a restriction site providing an insertion site for the DNA sequences encoding the heterologous polypeptide, wherein the restriction site is located 3' of the leader ribosome binding site as a substitute for the Taq I site of the trp promoter-operator and is selected from the group consisting of Xba I and Eco RI. Also provided are *E. coli* strains transformed with the above described recombinant DNA vehicles.

12 Claims, 14 Drawing Sheets

BACTERIAL POLYPEPTIDE EXPRESSION EMPLOYING TRYPTOPHAN PROMOTER-OPERATOR

This is a continuation of application Ser. No. 07/655,215 filed Feb. 12, 1991, now abandoned, which is a continuation of application Ser. No. 07/076,253 filed Jul. 21 1987, now abandoned, which is a continuation of application Ser. No. 06/685,521 filed Dec. 24, 1984, now abandoned, which is a continuation of application Ser. No. 06/307,473 filed Oct. 1, 1981, now abandoned, which is a continuation of application Ser. No. 06/133,296 filed Mar. 24, 1980, now abandoned.

BACKGROUND OF THE INVENTION

With the advent of recombinant DNA technology, the controlled bacterial production of an enormous variety of useful polypeptides has become possible. Already in hand are bacteria modified by this technology to permit the production of such polypeptide products such as somatostatin (K. Itakura, et al., Science 198, 1056 [1977]), the (component) A and B chains of human insulin (D. V. Goeddel, et al., Proc Nat'l Acad Sci, USA 76, 106 [1979]), and human growth hormone (D. V. Goeddel, et al., Nature 281, 544 [1979]). More recently, recombinant DNA techniques have been used to occasion the bacterial production of thymosin alpha 1, an immune potentiating substance produced by the thymus (U.S. patent application of Roberto Crea and Ronald Wetzel, filed Feb. 28, 1980 and assigned to the assignee of the present application). Such is the power of the technology that virtually any useful polypeptide an be bacterially produced, putting within reach the controlled manufacture of hormones, enzymes, antibodies, and vaccines against a wide variety of diseases. The cited materials, which describe in greater detail the representative examples referred to above, are incorporated herein by reference, as are other publications referred to infra, to illuminate the background of the invention.

The work horse of recombinant DNA technology is the plasmid, a non-chromosomal loop of double-stranded DNA found in bacteria, oftentimes in multiple copies per bacterial cell. Included in the information encoded in the plasmid DNA is that required to reproduce the plasmid in daughter cells (i.e., a "replicon") and ordinarily, one or more selection characteristics, such as resistance to antibiotics, which permit clones of the host cell containing the plasmid of interest to be recognized and preferentially grown in selective media. The utility of bacterial plasmids lies in the fact that they can be specifically cleaved by one or another restriction endonuclease or "restriction enzyme", each of which recognizes a different site on the plasmidic DNA. Thereafter heterologous genes or gene fragments may be inserted into the plasmid by endwise joining at the cleavage site or at reconstructed ends adjacent the cleavage site. As used herein, the term "heterologous" refers to a gene not ordinarily found in, or a polypeptide sequence ordinarily not produced by, *E. coli,* whereas the term "homologous" refers to a gene or polypeptide which is produced in wild-type *E. coli.* DNA recombination is performed outside the bacteria, but the resulting "recombinant" plasmid can be introduced into bacteria by a process known as transformation and large quantities of the heterologous gene-containing recombinant plasmid obtained by growing the transformant. Moreover, where the gene is properly inserted with reference to portions of the plasmid which govern the transcription and translation of the encoded DNA message, the resulting expression vehicle can be used to actually produce the polypeptide sequence for which the inserted gene codes, a process referred to as expression.

Expression is initiated in a region known as the promoter which is recognized by and bound by RNA polymerase. In some cases, as in the trp operon discussed infra, promoter regions are overlapped by "operator" regions to form a combined promoter-operator. Operators are DNA sequences which are recognized by so-called repressor proteins which serve to regulate the frequency of transcription initiation at a particular promoter. The polymerase travels along the DNA, transcribing the information contained in the coding strand from its 5' to 3' end into messenger RNA which is in turn translated into a polypeptide having the amino acid sequence for which the DNA codes. Each amino acid is encoded by a unique nucleotide triplet or "codon" within what may for present purposes be referred to as the "structural gene", i.e. that part which encodes the amino acid sequence of the expressed product. After binding to the promoter, the RNA polymerase first transcribes nucleotides encoding a ribosome binding site, then a translation initiation or "start" signal (ordinarily ATG, which in the resulting messenger RNA becomes AUG), then the nucleotide codons within the structural gene itself. So-called stop codons are transcribed at the end of the structural gene whereafter the polymerase may form an additional sequence of messenger RNA which, because of the presence of the stop signal, will remain untranslated by the ribosomes. Ribosomes bind to the binding site provided on the messenger RNA, in bacteria ordinarily as the mRNA is being formed, and themselves produce the encoded polypeptide, beginning at the translation start signal and ending at the previously mentioned stop signal. The desired product is produced if the sequences encoding the ribosome binding site are positioned properly with respect to the AUG initiator codon and if all remaining codons follow the initiator codon in phase. The resulting product may be obtained by lysing the host cell and recovering the product by appropriate purification from other bacterial protein.

Polypeptides expressed through the use of recombinant DNA technology may be entirely heterologous, as in the case of the direct expression of human growth hormone, or alternatively may comprise a heterologous polypeptide and, fused thereto, at least a portion of the amino acid sequence of a homologous peptide, as in the case of the production of intermediates for somatostatin and the components of human insulin. In the latter cases, for example, the fused homologous polypeptide comprised a portion of the amino acid sequence for beta galactosidase. In those cases, the intended bioactive product is bioinactivated by the fused, homologous polypeptide until the latter is cleaved away in an extracellular environment. Fusion proteins like those just mentioned can be designed so as to permit highly specific cleavage of the precusor protein from the intended product, as by the action of cyanogen bromide on methionine, or alternatively by enzymatic cleavage. See, eg., G.B. Patent Publication No. 2 007 676 A.

If recombinant DNA technology is to fully sustain its promise, systems must be devised which optimize expression of gene inserts, so that the intended polypeptide products can be made available in high yield. The beta lactamase and lactose promoter-operator systems most commonly used in the past, while useful, have not fully utilized the capacity of the technology from the standpoint of yield. A need has existed for a bacterial expression vehicle capable of the controlled expression of desired polypeptide products in higher yield.

Tryptophan is an amino acid produced by bacteria for use as a component part of homologous polypeptides in a biosynthetic pathway which proceeds: chorismic acid→anthranilic acid→phosphoribosyl antranilic acid→CDRP [enol-1-(o-carboxyphenylamino)-1-desoxy-D-ribulose-5-phosphate]→indol-3-glycerol-phosphate, and ultimately to tryptophan itself. The enzymatic reactions of this pathway are catalyzed by the products of the tryptophan or "trp" operon, a polycistronic DNA segment which is transcribed under the direction of the trp promoter-operator system. The resulting polycistronic messenger RNA encodes the so-called trp leader sequence and then, in order, the polypeptides referred to as trp E, trp D, trp C, trp B and trp A. These polypeptides variously catalyze and control individual steps in the pathway chorismic acid tryptophan.

In wild-type *E. coli*, the tryptophan operon is under at least three distinct forms of control. In the case of promoter-operator repression, tryptophan acts as a corepressor and binds to its aporepressor to form an active repressor complex which, in turn, binds to the operator, closing down the pathway in its entirety. Secondly, by a process of feedback inhibition, tryptophan binds to a complex of the trp E and trp D polypeptides, prohibiting their participation in the pathway synthesis. Finally, control is effected by a process known as attenuation under the control of the "attenuator region" of the gene, a region within the trp leader sequence. See generally G. F. Miozzari et al, *J. Bacteriology* 133, 1457 (1978); *The Operon* 263–302, Cold Spring Harbor Laboratory (1978), Miller and Reznikoff, eds.; F. Lee et al, *Proc. Natl. Acad. Sci. USA*, 74, 4365 (1977) and K. Bertrand et al, *J. Mol. Biol.* 103, 319 (1976). The extent of attenuation appears to be governed by the intracellular concentration of tryptophan, and in wild-type *E. coli* the attenuator terminates expression in approximately nine out of ten cases, possibly through the formation of a secondary structure, or "termination loop", in the messenger RNA which causes the RNA polymerase to prematurely disengage from the associated DNA.

Other workers have employed the trp operon to obtain some measure of heterologous polypeptide expression. This work, it is believed, attempted to deal with problems of repression and attenuation by the addition of indole acrylic acid, an inducer and analog which competes with tryptophan for trp repressor molecules, tending toward derepression by competitive inhibition. At the same time the inducer diminishes attenuation by inhibiting the enzymatic conversion of indole to tryptophan and thus effectively depriving the cell of tryptophan. As a result more polymerases successfully read through the attentuator. However, this approach appears problematic from the standpoint of completing translation consistently and in high yield, since tryptophan-containing protein sequences are prematurely terminated in synthesis due to lack of utilizable tryptophan. Indeed, an effective relief of attenuation by this approach is entirely dependent on severe tryptophan starvation.

The present invention addresses problems associated with tryptophan repression and attenuation in a different manner and provides (1) a method for obtaining an expression vehicle designed for direct expression of heterologous genes from the trp promoter-operator, (2) methods for obtaining vehicles designed for expression, from the tryptophan operator-promoter, of specifically cleavable polypeptides coded by homologous-heterologous gene fusions and (3) a method of expressing heterologous polypeptides controllably, efficiently and in high yield, as well as the associated means.

SUMMARY OF THE INVENTION

According to the present invention novel plasmidic expression vehicles are provided for the production in bacteria of heterologous polypeptide products, the vehicles having a sequence of double-stranded DNA comprising, in phase from a first 5' to a second 3' end of the coding strand, a trp promoter-operator, nucleotides coding for the trp leader ribosome binding site, and nucleotides encoding translation initiation for expression of a structural gene that encodes the amino acid sequence of the heterlogous polypeptide. The DNA sequence referred to contains neither a trp attenuator region nor nucleotides coding for the trp E ribosome binding site. Instead, the trp leader ribosome binding site is efficiently used to effect expression of the information encoded by an inserted gene.

Cells are transformed by addition of the trp promoter-operator-containing and attenuator-lacking plasmids of the invention and grown up in the presence of additive tryptophan. The use of tryptophan-rich media provides sufficient tryptophan to essentially completely repress the trp promoter-operator through trp/repressor interactions, so that cell growth can proceed uninhibited by premature expression of large quantities of heterologous polypeptide encoded by an insert otherwise under the control of the trp promoter-operator system. When the recombinant culture has been grown to the levels appropriate for industrial production of the polypeptide, on the other hand, the external source of tryptophan is removed, leaving the cell to rely only on the tryptophan that it can itself produce. The result is mild tryptophan limitation and, accordingly, the pathway is derepressed and highly efficient expression of the heterologous insert occurs, unhampered by attenuation because the attenuator region has been deleted from the system. In this manner the cells are never severely deprived of tryptophan and all proteins, whether they contain tryptophan or not, can be produced in substantial yields.

The invention further provides means of cleaving double-stranded DNA at any desired point, even absent a restriction enzyme site, a technique useful in, among other things, the creation of trp operons having attenuator deletions other than those previously obtained by selection of mutants.

Finally, the invention provides a variety of useful intermediates and endproducts, including specifically cleavable heterologous-homologous fusion proteins that are stabilized against degradation under expression conditions.

The manner in which these and other objects and advantages of the invention are obtained will become more apparent from the detailed description which follows and from the accompanying drawings in which.

Figure 1:
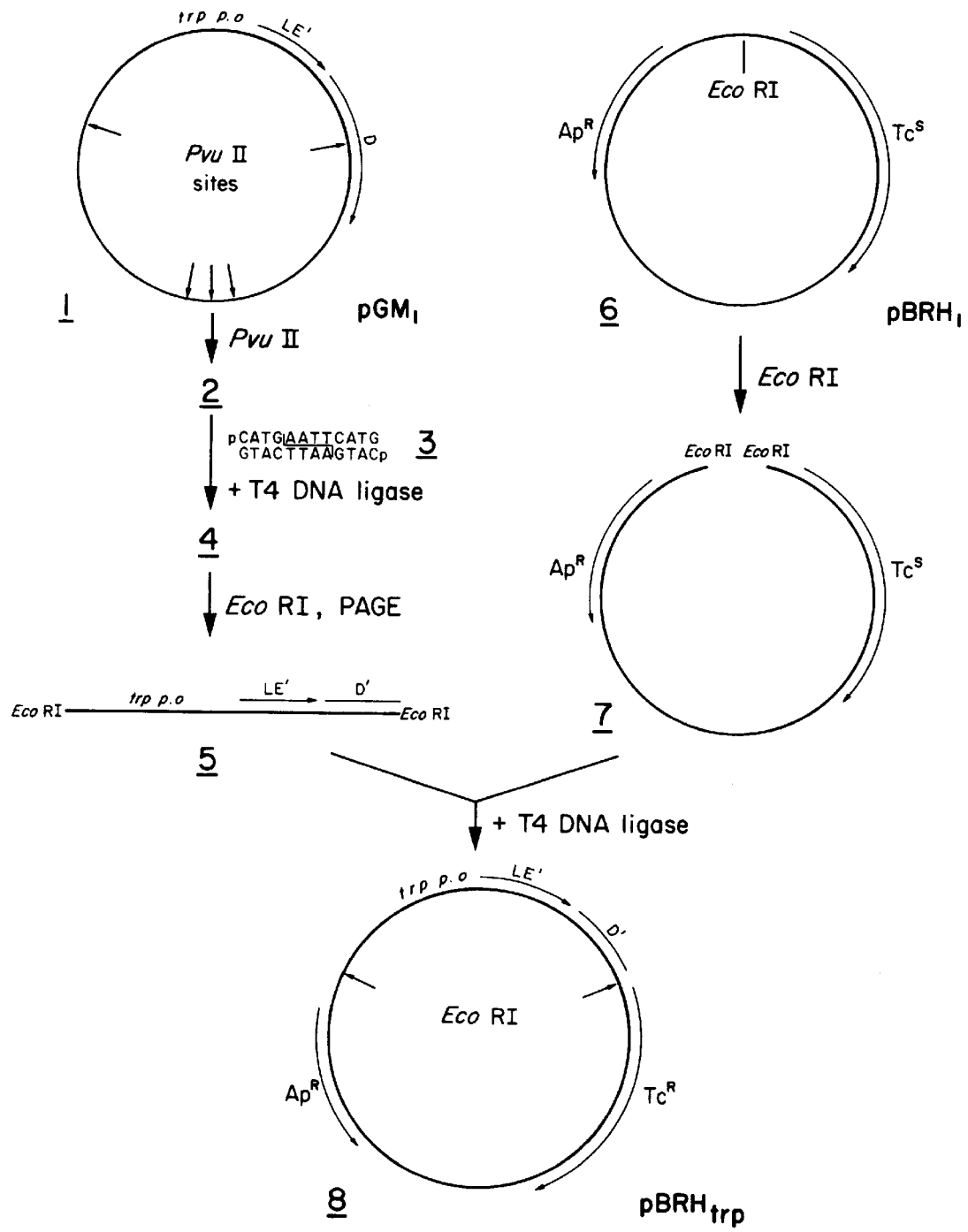
FIGS. 1 and 2 illustrate a preferred scheme for forming plasmids capable of expressing heterologous genes as fusions with a portion of the trp D polypeptide, from which fusion they may be later cleaved.

In the Figures, only the coding strand of the double-stranded plasmid and linear DNAs are depicted in most instances, for clarity in illustration. Antibiotic resistance-encoding genes are denoted $ap^R$ (ampicillin) and $tc^R$ (tetracycline). The legend $tc^S$ connotes a gene for tetracycline resistance that is not under the control of a promoter-operator system, such that plasmids containing the gene will nevertheless be tetracycline sensitive. The legend "$ap^S$" connotes ampicillin sensitivity resulting from deletion of a portion of the gene encoding ampicillin sensitivity. Plasmidic promoters and operators are denoted "p" and "o". The letters A, T, G and C respectively connote the nucleotides containing the bases adenine, thymine, guanine and cytosine. Other Figure legends appear from the text.

The preferred embodiments of the invention described below involved use of a number of commonly available restriction endonucleases next identified, with their corresponding recognition sequences and (indicated by arrow) cleavage patterns.

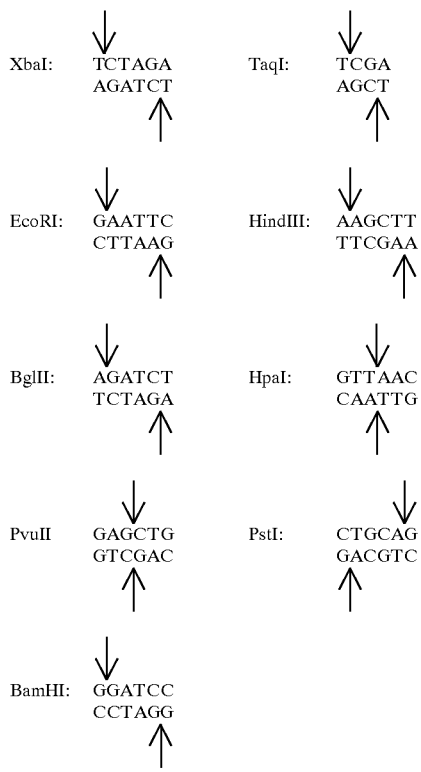

Where the points of cleavage are spaced apart on the respective strands the cleaved ends will be "sticky", ie, capable of reannealing or of annealing to other complementarily "sticky"-ended DNA by Watson-Crick base pairing (A to T and G to C) in mortise and tenon fashion. Some restriction enzymes, such as HpaI and PvuII above, cleave to leave "blunt" ends. The nucleotide sequences above are represented in accordance with the convention used throughout: upper strand is the protein encoding strand, and in proceeding from left to right on that strand one moves from the 5' to the 3' end thereof, ie, in the direction of transcription from a "proximal" toward a "distal" point.

Finally with regard to conventions, the symbol "Δ" connotes a deletion. Thus, for example, reference to a plasmid followed by, say, "ΔEcoRI-XbaI" describes the plasmid from which the nucleotide sequence between EcoRI and XbaI restriction enzyme sites has been removed by digestion with those enzymes. For convenience, certain deletions are denoted by number. Thus, beginning from the first base pair ("bp") of the EcoRI recognition site which precedes the gene for tetracycline resistance in the parental plasmid pBR322, "Δ31" connotes deletion of bp1–30 (ie, ΔEcoRI-Hind III) and consequent disenabling of the tetracycline promoter-operator system; "Δ2" connotes deletion of bp 1–375 (ie, ΔEcoRI-BamHI) and consequent removal of both the tetracycline promoter-operator and the structural gene which encodes tetracycline resistance; and "Δ3" connotes deletion of bp 3611–4359 (ie, ΔPstI-EcoRI) and elimination of ampicillin resistance. "Δ4" is used to connote removal of bp ~900–~1500 from the trp operon fragment 5 (FIG. 1), eliminating the structural gene for the trp D polypeptide.

DETAILED DESCRIPTION

The trp leader sequence is made up of base pairs ("bp") 1–162, starting from the start point for trp mRNA. A fourteen amino acid putative trp leader polypeptide is encoded by bp 27–71 following the ATG nucleotides which encode the translation start signal. The trp attenuator region comprises successive GC-rich and AT-rich sequences lying between bp 114 and 156 and attenuation is apparently effected on mRNA nucleotides encoded by bp ~134–141 of the leader sequence. To express a heterologous polypeptide under the direction of the trp leader ribosome binding site and at the same time avert attenuation, the following criteria must be observed:

1. Base pairs 134–141 or beyond must be deleted;
2. The ATG codon of the inserted gene must be positioned in correct relation to a ribosome binding site, as is known (see, eg., J. A. Steitz "Genetic signals and nucleotide sequences in messenger RNA" in *Biological Regulation and Control* (ed. R. Goldberger) Plenum Press, New York (1978).
3. Where a homologous-heterologous fusion protein is to be produced, the translation start signal of a homologous polypeptide sequence should remain available, and the codons for the homologous portion of the fusion protein have to be inserted in phase without intervening translation stop signals.

For example, deleting all base pairs within the leader sequence distal from bp. 70 removes the attenuator region, leaves the ATG sequence which encodes the translation start signal, and eliminates the intervening translation stop encoded by TCA (bp. 69–71), by eliminating A and following nucleotides. Such a deletion would result in expression of a fusion protein beginning with the leader polypeptide, ending with that encoded by any heterologous insert, and including a distal region of one of the post-leader trp operon polypeptides determined by the extent of the deletion in the 3' direction. Thus a deletion extending into the E gene would lead to expression of a homologous precursor comprising the L sequence and the distal region of E (beyond the deletion endpoint) fused to the sequence encoded by any following insert, and so on.

Two particularly useful plasmids from which the attenuator region has been deleted are the plasmids pGM1 and pGM3, G. F. Miozzari et al, *J. Bacteriology* 133, 1457 (1978). These respectively carry the deletions trp ΔLE 1413 and trp ΔLE 1417 and express (under the control of the trp promoter-operator) a polypeptide comprising approximately the first six amino acids of the trip leader and distal regions of the E polypeptide. In the most preferred case, pGM1, only about the last third of the E polypeptide is expressed whereas pGM3 expresses almost the distal one half of the E polypeptide codons. *E. coli* K-12 strain W3110 tna 2⁻trp⁻Δ102 containing pGM1 has been deposited with the American Type Culture Collection (ATCC no. 31622). pGM1 may be conventionally removed from the strain for use in the procedures described below.

Alternatively, deletions may be effected by means provided by the invention for specifically cleaving double-stranded DNA at any desired site. One example of this cleavage technique appears from Part IV of the experimental section, infra. Thus, double-stranded DNA is converted to single-stranded DNA in the region surrounding the intended cleavage point, as by reaction with lambda exonuclease. A synthetic or other single-stranded DNA primer is then hybridized to the single-stranded length earlier formed, by Watson-Crick base-pairing, the primer sequence being such as to ensure that the 5' end thereof will be coterminous with the nucleotide on the first strand just prior to the intended cleavage point. The primer is next extended in the 3' direction by reaction with DNA polymerase, recreating that portion of the original double-stranded DNA prior to the intended cleavage that was lost in the first step. Simultaneously or thereafter, the portion of the first strand beyond the intended cleavage point is digested away. To summarize, where "v" marks the intended cleavage point:

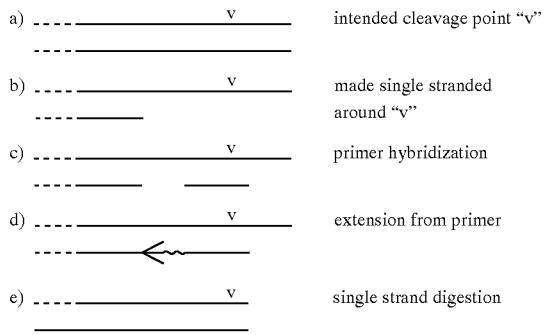

In the most preferred embodiment, steps (d) and (e) are performed simultaneously, using a polymerase that simultaneously digests the protruding single stranded end in the 3'→5' direction and extends the primer (in the presence of dATP, dGTP, dTTP and dCTP) in the 5'→3' direction. The material preferred for this purpose is Klenow Polymerase I, ie, that fragment obtained by proteolytic cleavage of DNA Polymerase I which contains the 5'→3' polymerizing activity and the 3'→5' exonucleolytic activity of the parental enzyme, yet lacks its 5'→3' exonucleolytic activity. A. Kornberg, *DNA Synthesis*, 98, W. H. Freeman and Co., SFO (1974).

Using the procedure just described, attenuator deletions may be made in any desired manner in a trp operon-containing plasmid first linearized by, eg, cleavage at a restriction site downstream from the point at which the molecule is to be blunt-ended ("v" above). Recircularization following deletion of the attenuator region may be effected, eg, by blunt end ligation or other manners which will be apparent to the art-skilled.

Although the invention encompasses direct expression of heterologous polypeptide under the direction of the trp promoter-operator, the preferred case involves expression of fused proteins containing both homologous and heterologous sequences, the latter preferably being specifically cleavable from the former in extra-cellular environs. Particularly preferred are fusions in which the homologous portion comprises one or more amino acids of the trp leader polypeptide and about one-third or more of the trp E amino acid sequence (distal end). Fusion proteins so obtained appear remarkably stabilized against degradation under expression conditions.

Bacteria *E. coli* K-12 strain W3110 tna 2⁻trp⁻Δ102 (pGM1), ATCC No. 31622, may be used to amplify stocks of the pGM1 plasmid preferably employed in constructing the attenuator-deficient trp promoter-operator systems of the invention. This strain is phenotypically trp⁺ in the presence of anthranilate and can be grown in minimal media such as LB supplemented with 50 μg/ml anthranilate.

All bacterial strains used in trp promoter-operator directed expression according to the invention are trp repressor⁺ ("trp R⁺") as in the case of wild-type *E. coli*, so as to ensure repression until heterologous expression is intended.

DNA recombination is, in the preferred embodiment, performed in *E. coli*, K-12 strain-294 (end A, thi⁻, hsr⁻, hsm⁺ₖ), ATCC No. 31446, a bacterial strain whose membrane characteristics facilitate transformations. Heterologous polypeptide-producing plasmids grown in strain 294 are conventionally extracted and maintained in solution (eg, 10 mM tris, 1 mM EDTA, pH8) at from about −20° C. to about 420 C. For expression under industrial conditions, on the other hand, we prefer a more hardy strain, ie, *E. coli* K-12 λ⁻F⁻ RV 308 str', gal 308⁻ ATCC No. 31608. RV 308 is nutritionally wild-type and grows well in minimal media, synthesizing all necessary macromolecules from conventional mixes of ammonium, phosphate and magnesium salts, trace metals and glucose. After transformation of RV 308 culture with strain 294-derived plasmid the culture is plated on media selective for a marker (such as antibiotic resistance) carried by the plasmid, and a transformant colony picked and grown in flask culture. Aliquots of the latter in 10% DMSO or glycerol solution (in sterile Wheaton vials) are shell frozen in an ethanol-dry ice bath and frozen at −80° C. To produce the encoded heterologous polypeptide the culture samples are grown up in media containing tryptophan so as to repress the trp promoter-operator and the system then deprived of additive tryptophan to occasion expression.

For the first stage of growth one may employ, for example, LB medium (J. H. Miller, *Experiments in Molecular Genetics*, 433, Cold Spring Harbor Laboratory 1972) which contains, per liter aqueous solution, 10 g Bacto tryptone, 5 g Bacto yeast extract and 10 g NaCl. Preferably, the inoculant is grown to optical density ("o.d.") of 10 or more (at 550 nM), more preferably to o.d. 20 or more, and most preferably to o.d. 30 or more, albeit to less than stationary phase.

For derepression and expression the inoculant is next grown under conditions which deprive the cell of additive tryptophan. One appropriate media for such growth is M9. (J. H. Miller, supra at 431) prepared as follows (per liter):

KH₂PO₄ 3 g
Na₂HPO₄ 6 g
NaCl 0.5 g
NH₄Cl 1 g
Autoclave, then add:
10 ml 0.01 M CaCl₂

1 ml 1 M MgSO$_4$
10 ml 20% glucose
Vitamin B1 μg/ml
Humko hycase amino
or DIFCO cas. amino acids 40 μg/ml.

The amino acid supplement is a tryptophan-lacking acid hydrolysate of casein.

To commence expression of the heterologous polypeptide the inoculant grown in tryptophan-rich media may, eg, be diluted into a larger volume of medium containing no additive tryptophan (for example, 2–10 fold dilution) grown up to any desired level (preferably short of stationary growth phase) and the intended product conventionally obtained by lysis, centrifugation and purification. In the tryptophan-deprived growth stage, the cells are preferably grown to od in excess of 10, more preferably in excess of od 20 and most preferably to or beyond od 30 (all at 550 mM) before product recovery.

All DNA recombination experiments described in the Experimental section which follows were conducted at Genentech Inc. in accordance with the National Institutes of Health Guidelines for Recombinant DNA research.

I. Expression of D-polypeptide fusion protein

A preferred method of expressing fusion proteins comprising desired polypeptides and, fused thereto, a portion of the amino acid sequence of the trp D polypeptide that is separable in vitro by virtue of a methionine amino acid specifically sensitive to CNBr cleavage, is described with reference to FIGS. 1–3.

A. Construction of pBRHtrp

Plasmid pGM1 (1, FIG. 1) carries the *E. coli* tryptophan operon containing the deletion ΔLE1413 (G. F. Miozzari, et al., (1978) *J. Bacteriology* 1457–1466)) and hence expresses a fusion protein comprising the first 6 amino acids of the trp leader and approximately the last third of the trp E polypeptide (hereinafter referred to in conjunction as LE'), as well as the trp D polypeptide in its entirety, all under the control of the trp promoter-operator system. The plasmid, 20 μg, was digested with the restriction enzyme PvuII which cleaves the plasmid at five sites. The gene fragments 2 were next combined with EcoRI linkers (consisting of a self complementary oligonucleotide 3 of the sequence: pCATGAATTCATG) providing an EcoRI cleavage site for a later cloning into a plasmid containing an EcoRI site (20). The 20 μg of DNA fragments 2 obtained from pGM1 were treated with 10 units T$_4$ DNA ligase in the presence of 200 pico moles of the 5'-phosphorylated synthetic oligonucleotide pCATGAATTCATG (3) and in 20 μl T$_4$ DNA ligase buffer (20 mM tris, pH 7.6, 0.5 mM ATP, 10 mM MgCl$_2$, 5 mM dithiothreitol) at 4° C. overnight. The solution was then heated 10 minutes at 70° C. to halt ligation. The linkers were cleaved by EcoRI digestion and the fragments, now with EcoRI ends were separated using 5 percent polyacrylamide gel electrophoresis (herein after "PAGE") and the three largest fragments isolated from the gel by first staining with ethidium bromide, locating the fragments with ultraviolet light, and cutting from the gel the portions of interest. Each gel fragment, with 300 microliters 0.1xTBE, was placed in a dialysis bag and subjected to electrophoresis at 100 v for one hour in 0.1xTBE buffer (TBE buffer contains: 10.8 gm tris base, 5.5 gm boric acid, 0.09 gm Na$_2$EDTA in 1 liter H$_2$O ). The aqueous solution was collected from the dialysis bag, phenol extracted, chloroform extracted and made 0.2 M sodium chloride, and the DNA recovered in water after ethanol precipitation. [All DNA fragment isolations hereinafter described are performed using PAGE followed by the electroelution method just discussed]. The trp promoter-operator-containing gene with EcoRI sticky ends 5 was identified in the procedure next described, which entails the insertion of fragments into a tetracycline sensitive plasmid 6 which, upon promoter-operator insertion, becomes tetracycline resistant.

B. Creation of the plasmid pBRHtrp expressing tetracycline resistance under the control of the trp promoter-operator and identification and amplification of the trp promoter-operator containing DNA fragment 5 isolated in (A.) above.

Plasmid pBRH1 (6), (R. I. Rodriguez, et al., Nucleic Acids Research 6, 3267–3287 [1979]) expresses ampicilin resistance and contains the gene for tetracycline resistance but, there being no associated promoter, does not express that resistance. The plasmid is accordingly tetracycline sensitive. By introducing a promoter-operator system in the EcoRI site, the plasmid can be made tetracycline resistant.

pBRH1 was digested with EcoRI and the enzyme removed by phenol extraction followed by chloroform extraction and recovered in water after ethanol precipitation. The resulting DNA molecule 7 was, in separate reaction mixtures, combined with each of the three DNA fragments obtained in part A. above and ligated with T$_4$ DNA ligase as previously described. The DNA present in the reaction mixture was used to transform competent *E. coli* K-12 strain 294, K. Backman et al., Proc Nat'l Acad Sci USA 73, 4174–4198 [1976]) (ATCC no. 31448) by standard techniques (V. Hershfield et al., Proc Nat'l Acad Sci USA 71, 3455–3459 [1974]) and the bacteria plated on LB plates containing 20 μg/ml ampicillin and 5 μg/ml tetracycline. Several tetracycline-resistant colonies were selected, plasmid DNA isolated and the presence of the desired fragment confirmed by restriction enzyme analysis. The resulting plasmid 8, designated pBRHtrp, expresses β-lactamase, imparting ampicillin resistance, and it contains a DNA fragment including the trp promoter-operator and encoding a first protein comprising a fusion of the first six amino acids of the trp leader and approximately the last third of the trp E polypeptide (this polypeptide is designated LE'), and a second protein corresponding to approximately the first half of the trp D polypeptide (this polypeptide is designated D'), and a third protein coded for by the tetracycline resistance gene.

C. Cloning genes for various end-product polypeptides and expression of these as fusion proteins comprising end-product and specifically cleavable trp D polypeptide precursor (FIG. 2).

Figure 2:
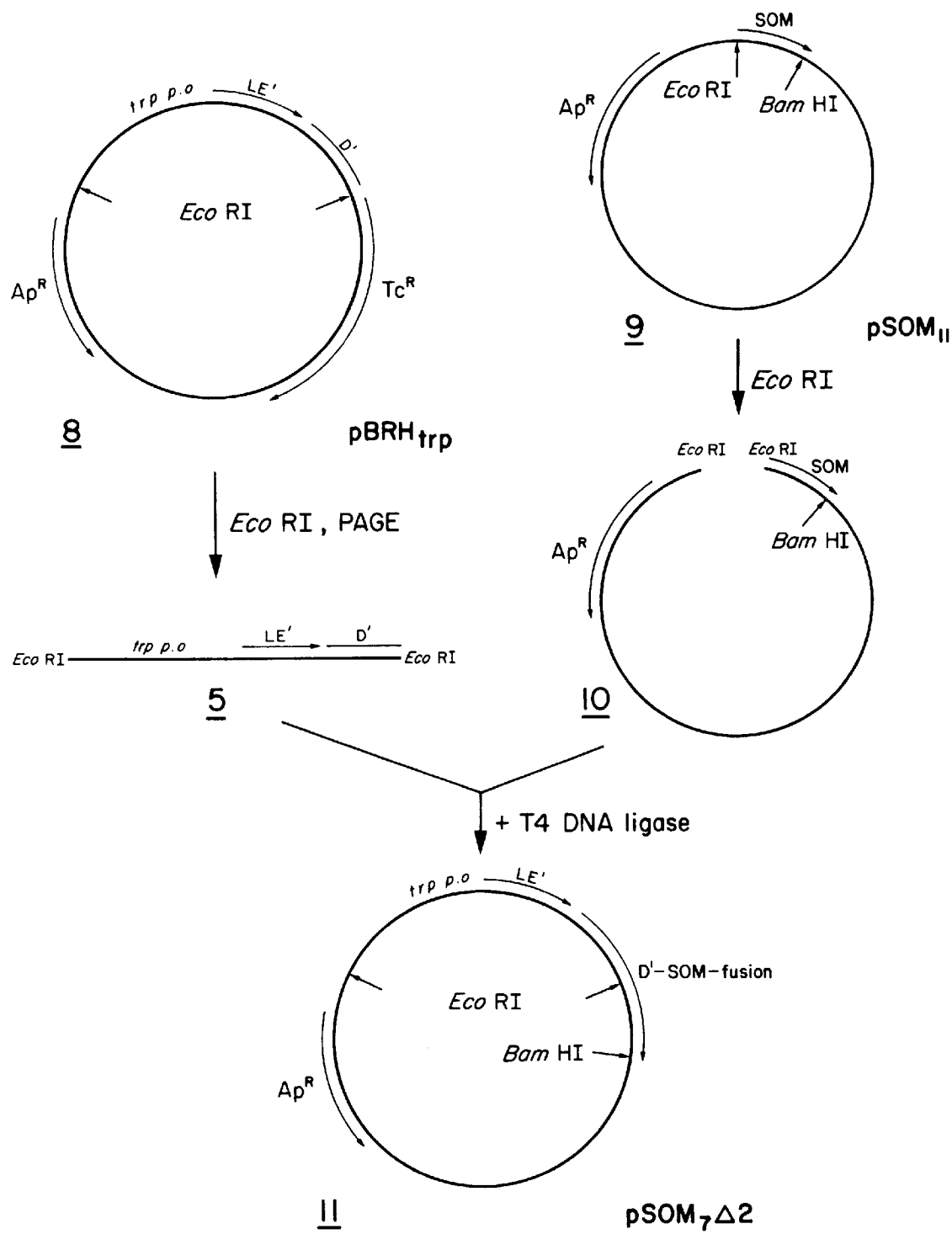

A DNA fragment comprising the trp promoter-operator and codons for the LE' and D' polypeptides was obtained from plasmid pBRHtrp and inserted into plasmids containing structural genes for various desired polypeptides, next exemplified for the case of somatostatin (FIG. 2).

pBRH trp was digested with EcoRI restriction enzyme and the resulting fragment 5 isolated by PAGE and electroelution. EcoRI-digested plasmid pSom 11 ( K. Itakura et al, *Science* 198, 1056 (1977); G.B. patent publication no. 2 007 676 A) was combined with fragment 5. The mixture was ligated with T$_4$ DNA ligase as previously described and the resulting DNA transformed into *E. coli* K-12 strain 294 as previously described. Transformant bacteria were selected on ampicillin-containing plates. Resulting ampicillin-resistant colonies were screened by colony hybridization (M. Gruenstein et al., Proc Nat'l Acad Sci USA 72, 3951–3965 [1975]) using as a probe the trp promoteroperator-containing fragment 5 isolated from pBRHtrp, which had been radioactively labelled with p³². Several colonies shown positive by colony hybridization were selected, plasmid DNA was isolated and the orientation of the inserted fragments determined by restriction analysis employing restriction enzymes BglII and BamHI in double digestion. E. coli 294 containing the plasmid designated pSOM7Δ2, 11, which has the trp promoter-operator fragment in the desired orientation was grown in LB medium containing 10 μg/ml ampicillin. The cells were grown to optical density 1 (at 550 nM), collected by centrifugation and resuspended in M9 media in tenfold dilution. Cells were grown for 2–3 hours, again to optical density 1, then lysed and total cellular protein analyzed by SDS (sodium dodcyl sulfate) urea (15 percent) polyacrylamide gel electrophoresis (J. V. Maizel Jr. et al., Meth Viral 5, 180–246 [1971]).

Figure 3:
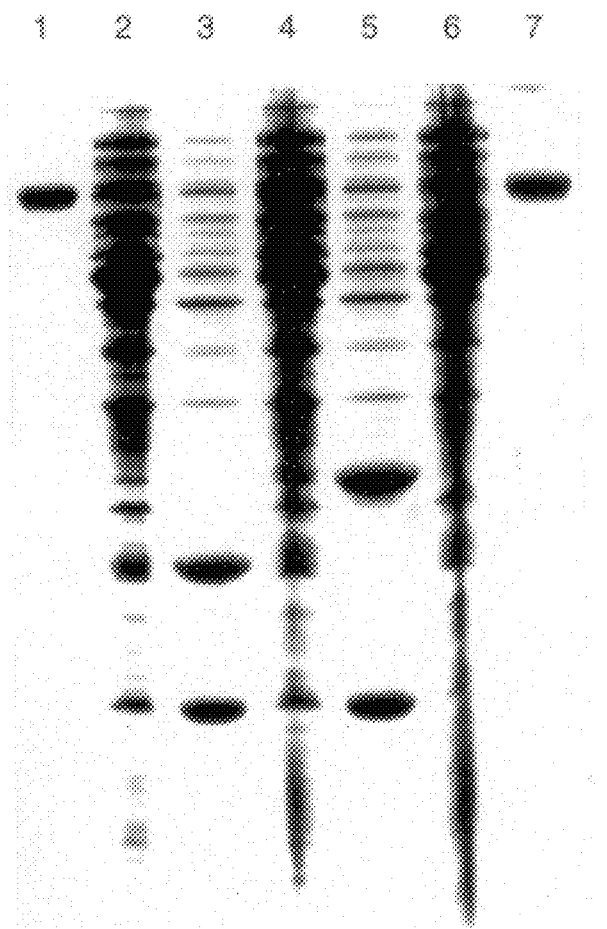
FIG. 3 is the result of polyacrylamide gel segregation of cell protein containing homologous (trp D')-heterologous (somatostatin or thymosin α 1) fusion proteins.

FIG. 3 illustrates a protein gel analysis in which total protein from various cultures is separated by size. The density of individual bands reflects the quantity in which the respective proteins are present. With reference to FIG. 3, lanes 1 and 7 are controls and comprise a variety of proteins of previously determined size which serve as points of comparative reference. Lanes 2 and 3 segregate cellular protein from colonies of E. coli 294 transformed with plasmid pSom7 Δ2 and respectively grown in LB (lane 2) and M9 (lane 3) media. Lanes 4 and 5 segregate cellular protein obtained from similar cells transformed with the plasmid pThα7 Δ2, a thymosin expression plasmid obtained by procedures essentially identical to those already described, beginning with the plasmid pThα1 (see the commonly assigned U.S. patent application of Roberto Crea and Ronald B. Wetzel, filed Feb. 28, 1980 for Thymosin Alpha 1 Production, the disclosure of which is incorporated herein by reference). Lane 4 segregates cellular protein from E. coli 294/pThα7 Δ2 grown in LB media, whereas lane 5 segregates cell protein from the same transformant grown in M9 media. Lane 6, another control, is the protein pattern of E. coli 294/pBR322 grown in LB.

Comparison to controls shows the uppermost of the two most prominent bands in each of lanes 3 and 5 to be proteins of size anticipated in the case of expression of a fusion protein comprising the D' polypeptide and, respectively, somatostatin and thymosin (the other prominent band represents the LE' polypeptide resulting from deletion of the attenuator). FIG. 3 confirms that expression is repressed in tryptophan-rich media, but derepressed under tryptophan deficient conditions.

D. Cyanogen bromide cleavage and radioimmunoassay for hormone product

For both the thymosin and somatostatin cases, total cellular protein was cyanogen bromide-cleaved, the cleavage product recovered and, after, drying, was resuspended in buffer and analyzed by radioimmunoassay, confirming the expression of product immunologically identical, respectively, to somatostatin and thymosin. Cyanogen bromide cleavage was as described in D. V. Goeddel et al., Proc Nat'l Acad Sci USA 76, 106–110 [1979]).

II. Construction of plasmids for direct expression of heterologous genes under control of the trp promoter-operator system The strategy for direct expression entailed creation of a plasmid containing a unique restriction site distal from all control elements of the trp operon into which heterologous genes could be cloned in lieu of the trp leader sequence and in proper, spaced relation to the trp leader polypeptide's ribosome binding site. The direct expression approach is next exemplified for the case of human growth hormone expression.

Figure 4:
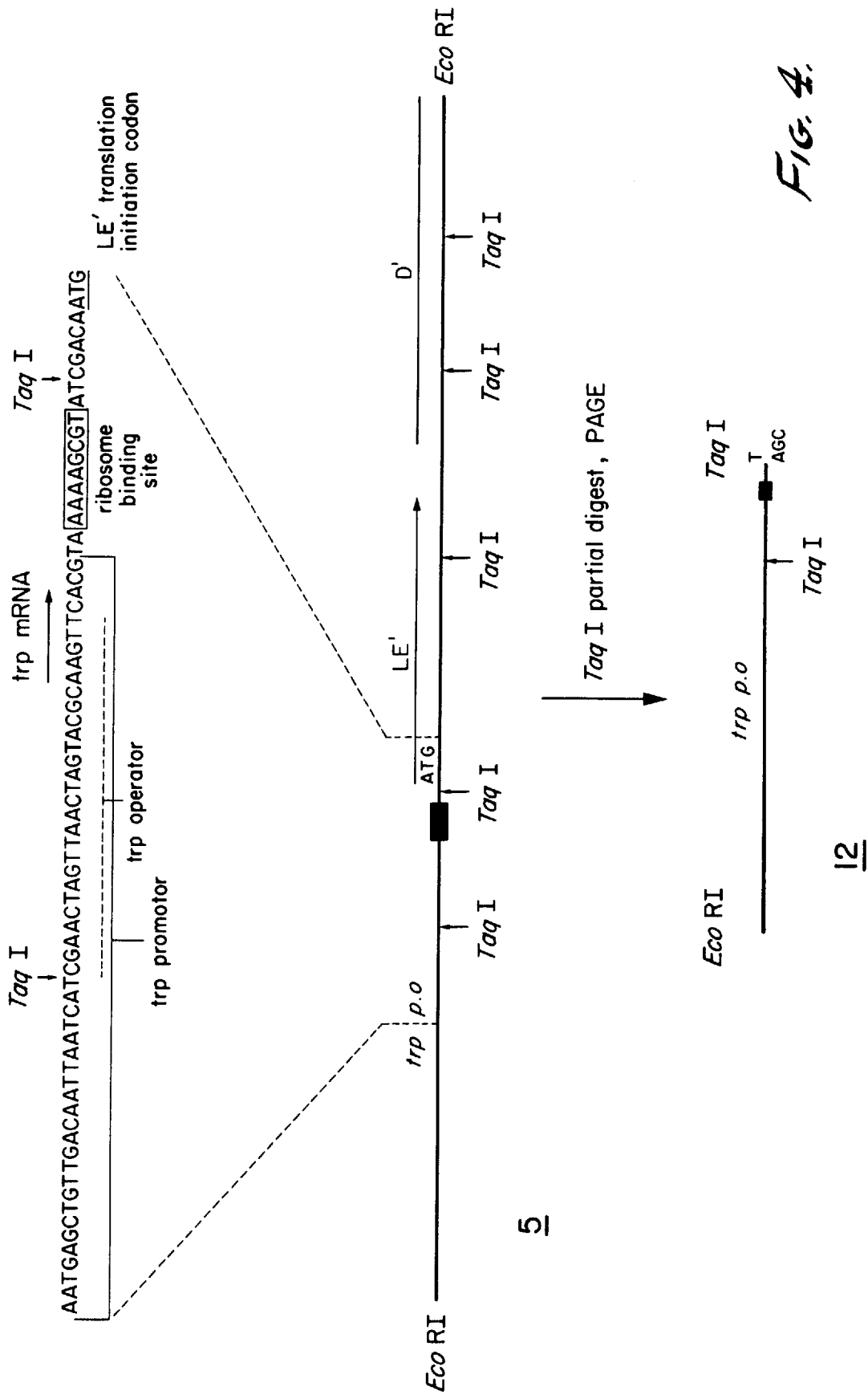
FIGS. 4, 5 and 6 illustrate successive stages in a preferred scheme for the creation of a plasmid capable of directly expressing a heterologous gene (human growth hormone) under the control of the trp promoter-operator system.

The plasmid pSom7 Δ2, 10 μg, was cleaved with EcoRI and the DNA fragment 5 containing the tryptophan genetic elements was isolated by PAGE and electroelution. This fragment, 2 μg, was digested with the restriction endonuclease Taq I, 2 units, 10 minutes at 37° C. such that, on the average, only one of the approximately five Taq I sites in each molecule is cleaved. This partially digested mixture of fragments was separated by PAGE and an approximately 300 base pair fragment 12 (FIG. 4) that contained one EcoRI end and one Taq I end was isolated by electroelution. The corresponding Taq I site is located between the transcription start and translation start sites and is 5 nucleotides upstream from the ATG codon of the trp leader peptide. The DNA sequence about this site is shown in FIG. 4. By proceeding as described, a fragment could be isolated containing all control elements of the trp operon, i.e., promoter-operator system, transcription initiation signal, and trp leader ribosome binding site.

Figure 5:
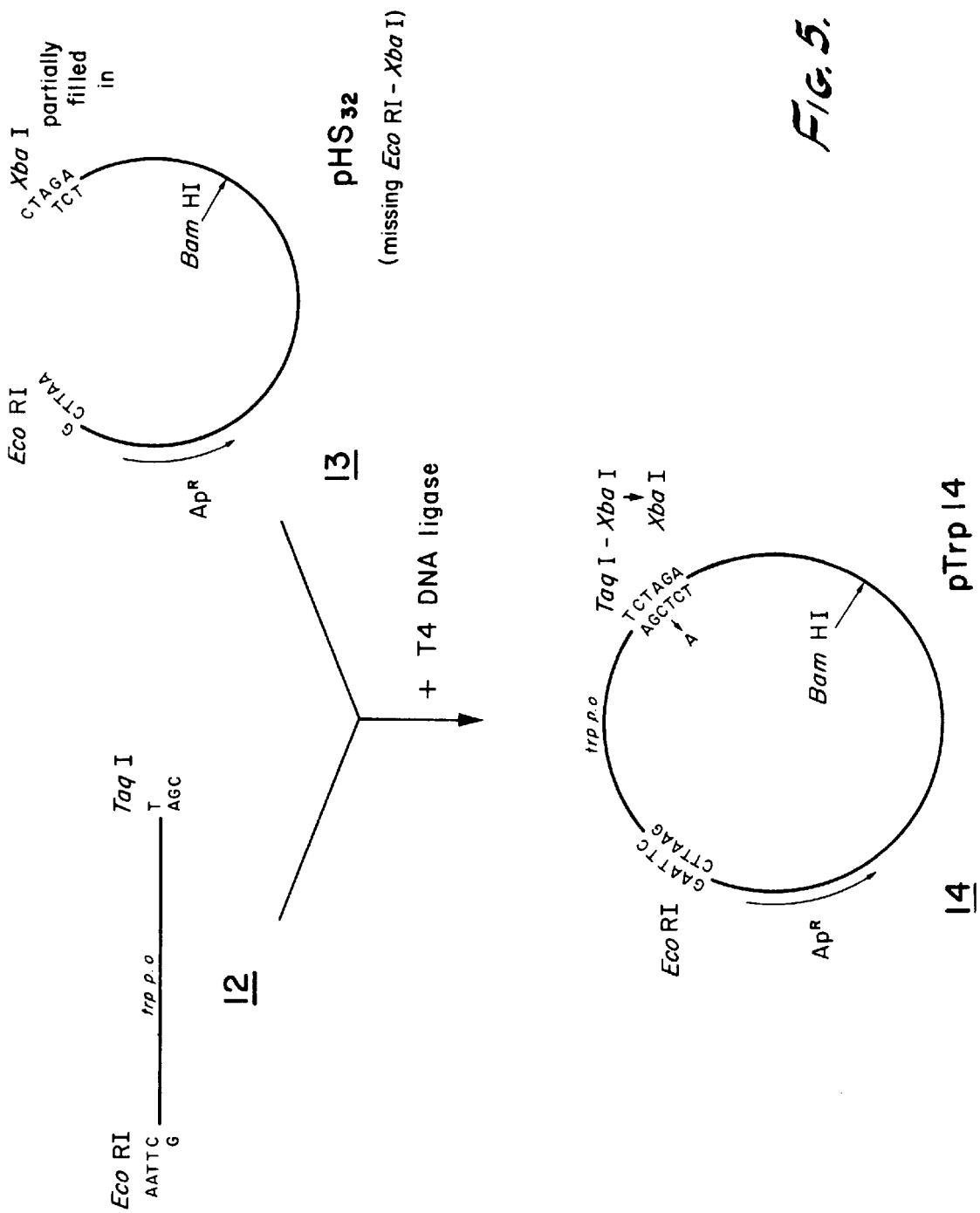

The Taq I residue at the 3' end of the resulting fragment adjacent the translation start signal for the trp leader sequence was next converted into an XbaI site, as shown in FIG. 5. This was done by ligating the fragment 12 obtained above to a plasmid containing a unique (i.e., only one) EcoRI site and a unique XbaI site. For this purpose, one may employ essentially any plasmid containing, in order, a replicon, a selectable marker such as antibiotic resistance, and EcoRI, XbaI and BamHI sites. Thus, for example, an XbaI site can be introduced between the EcoRI and BamHI sites of pBR322 (F. Bolivar et al., Gene 2, 95–119 [1977]) by, e.g., cleaving at the plasmid's unique Hind III site with Hind III followed by single strand-specific nuclease digestion of the resulting sticky ends, and blunt end ligation of a self annealing double-stranded synthetic nucleotide containing the recognition site such as CCTCTAGAGG. Alternatively, naturally derived DNA fragments may be employed, as was done in the present case, that contain a single XbaI site between EcoRI and BamHI cleavage residues. Thus, an EcoRI and BamHI digestion product of the viral genome of hepatitis B was obtained by conventional means and cloned into the EcoRI and BamHI sites of plasmid pGH6 (D. V. Goeddel et al., Nature 281, 544 [1979])) to form the plasmid pHS32. Plasmid pHS32 was cleaved with XbaI, phenol extracted, chloroform extracted and ethanol precipitated. It was then treated with 1 μl E. coli polymerase I, Klenow fragment (Boehringer-Mannheim) in 30 μl polymerase buffer (50 mM potassium phosphate pH 7.4, 7 mM MgCl₂, 1 mM β-mercaptoethanol) containing 0.1 mM dTTP and 0.1 mM dCTP for 30 minutes at 0° C. then 2 hr. at 37° C. This treatment causes 2 of the 4 nucleotides complementary to the 5' protruding end of the XbaI cleavage site to be filled in:

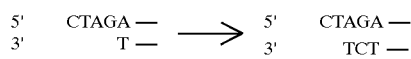

Two nucleotides, dC and dT, were incorporated giving an end with two 5' protruding nucleotides. This linear residue of plasmid pHS32 after phenol and chloroform extraction and recovery in water after ethanol precipitation) was cleaved with EcoRI. The large plasmid fragment 13 was separated from the smaller EcoRI-XbaI fragment by PAGE and isolated after electroelution. This DNA fragment from pHS32 (0.2 μg), was ligated, under conditions similar to those described above, to the EcoRI-Taq I fragment of the tryptophan operon (~0.01 μg), as shown in FIG. 5. In this process the Taq I protruding end is ligated to the XbaI remaining protruding end even though it is not completely Watson-Crick base-paired:

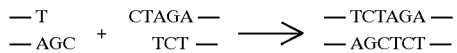

A portion of this ligation reaction mixture was transformed into *E. coli* 294 cells as in part I. above, heat treated and plated on LB plates containing ampicillin. Twenty-four colonies were selected, grown in 3 ml LB media, and plasmid isolated. Six of these were found to have the XbaI site regenerated via *E. coli* catalyzed DNA repair and replication:

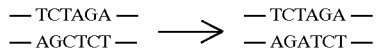

These plasmids were also found to cleave both with EcoRI and HpaI and to give the expected restriction fragments. One plasmid 14, designated pTrp 14, was used for expression of heterologous polypeptides, as next discussed.

Figure 6:
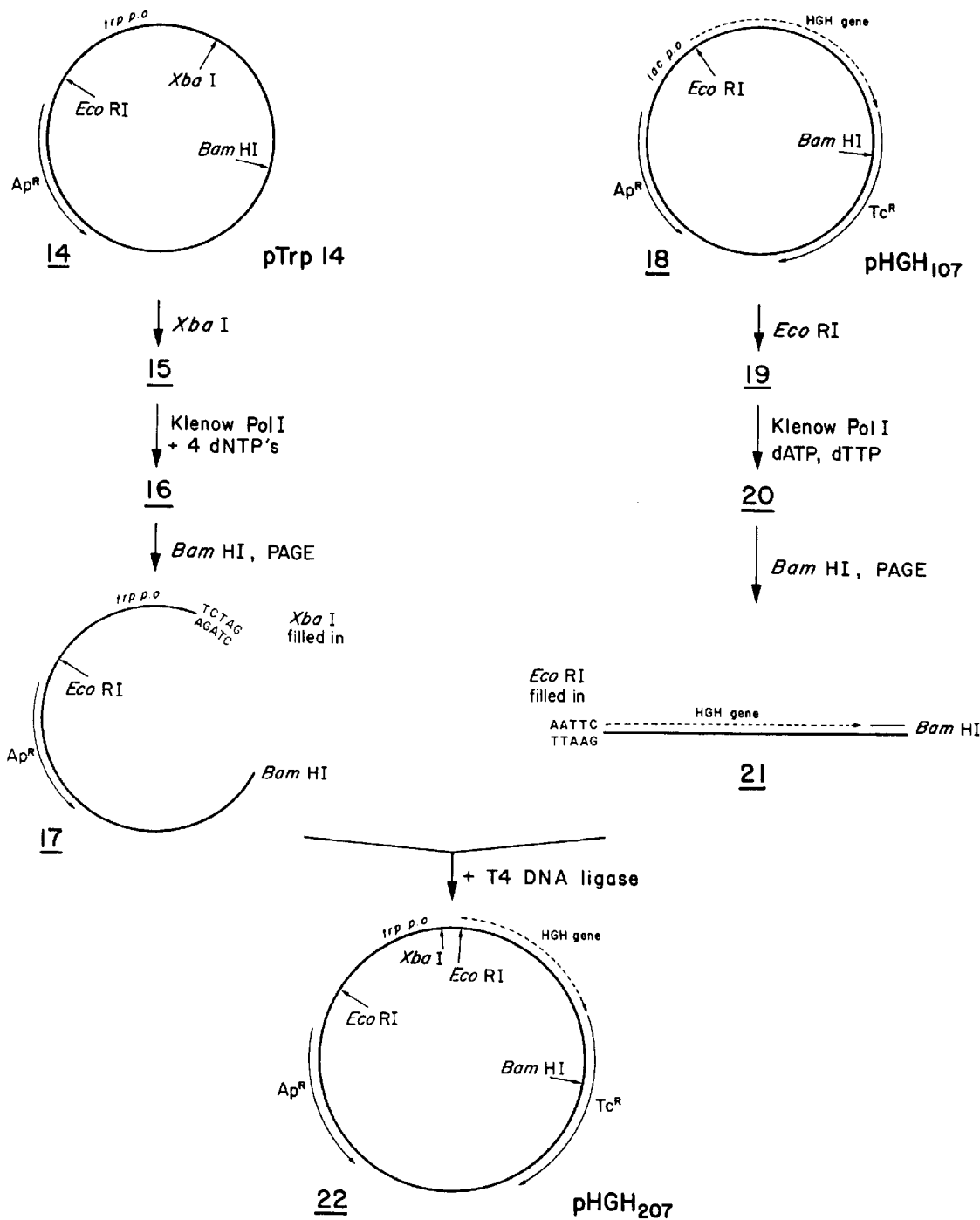

The plasmid pHGH 107 (18 in FIG. 6, D. V. Goeddel et al, *Nature,* 281, 544, 1979) contains a gene for human growth hormone made up of 23 amino acid codons produced from synthetic DNA fragments and 163 amino acid codons obtained from complementary DNA produced via reverse transcription of human growth hormone messenger RNA. This gene 21, though it lacks the codons of the "pre" sequence of human growth hormone, does contain an ATG translation initiation codon. The gene was isolated from 10 μg pHGH 107 after treatment with EcoRI followed by *E. coli* polymerase I Klenow fragment and dTTP and dATP as described above. Following phenol and chloroform extraction and ethanol precipitation the plasmid was treated with BamHI. See FIG. 6.

The human growth hormone ("HGH") gene-containing fragment 21 was isolated by PAGE followed by electroelution. The resulting DNA fragment also contains the first 350 nucleotides of the tetracycline resistance structural gene, but lacks the tetracyline promoter-operator system so that, when subsequently cloned into an expression plasmid, plasmids containing the insert can be located by the restoration of tetracycline resistance. Because the EcoRI end of the fragment 21 has been filled in by the Klenow polymerase I procedure, the fragment has one blunt and one sticky end, ensuring proper orientation when later inserted into an expression plasmid. See FIG. 6.

The expression plasmid pTrp14 was next prepared to receive the HGH gene-containing fragment prepared above. Thus, pTrp14 was XbaI digested and the resulting sticky ends filled in with the Klenow polymerase I procedure employing dATP, dTTP, dGTP and dCTP. After phenol and chloroform extraction and ethanol precipitation the resulting DNA 16 was treated with BamHI and the resulting large plasmid fragment 17 isolated by PAGE and electroelution. The pTrp14-derived fragment 17 had one blunt and one sticky end, permitting recombination in proper orientation with the HGH gene containing fragment 21 previously described.

The HGH gene fragment 21 and the pTrp14 ΔXba-BamHI fragment 17 were combined and ligated together under conditions similar to those described above. The filled in XbaI and EcoRI ends ligated together by blunt end ligation to recreate both the XbaI and the EcoRI site:

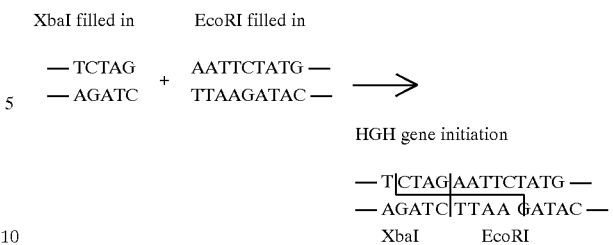

This construction also recreates the tetracycline resistance gene. Since the plasmid pHGH 107 expresses tetracycline resistance from a promoter lying upstream from the HGH gene (the lac promoter), this construction 22, designated pHGH 207, permits expression of the gene for tetracycline resistance under the control of the tryptophan promoter-operator. Thus the ligation mixture was transformed into *E. coli* 294 and colonies selected on LB plates containing 5 μg/ml tetracycline.

Figure 7:
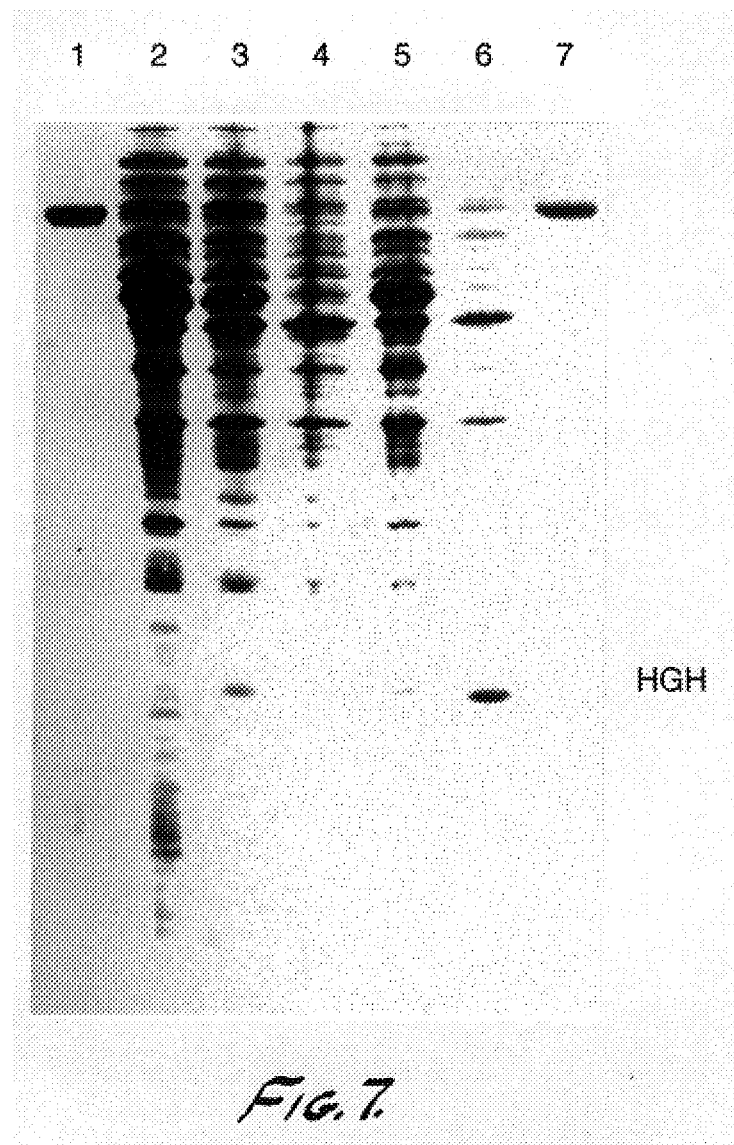
FIG. 7 is the result of polyacrylamide gel segregation of cell protein containing human growth hormone directly expressed under the control of the trp promoter-operator system.

In order to confirm the direct expression of human growth hormone from plasmid pHGH 207, total cellular protein derived from *E. coli* 294/pHGH 207 that had been grown to optical density 1 in LB media containing 10 μg/ml ampicillin and diluted 1 to 10 into M9 media, and grown again to optical density 1, was subjected to SDS gel electrophoresis as in the case of part I. above and compared to similar electrophoresis data obtained for human growth hormone as previously expressed by others (D. V. Goeddel et al, *Nature,* 281, 544 (1979)). FIG. 7 is a photograph of the resulting, stained gel wherein: Lanes 1 and 7 contain protein markers of various known sizes; Lane 2 is a control that separates total cellular protein of *E. Coli* strain 294 pBR322; Lane 3 segregates protein from *E. Coli* 294/pHGH 107 grown in LB media; Lane 4 segregates protein from *E. Coli* 294/pHGH 107 grown in M9 media; Lane 5 segregates protein from *E. Coli* 294/pHGH 207 grown in LB media; and Lane 6 segregates protein from *E. Coli* 294/pHGH 207 grown in M9. The dense band in Lane 6 is human growth hormone, as shown by comparison to the similar bands in Lanes 2–4. As predicted by the invention, the organism *E. Coli* 294/pHGH 207 when grown in tryptophan-rich LB media produces less human growth hormone by reason of tryptophan repressor/operator interactions, and when grown in M9 media produces considerably more HGH than *E. Coli* 294/pHGH 107 owing to the induction of the stronger tryptophan promoter-operator system vs the lac promoter-operator system in pHGH 107.

III. Creation of a general expression plasmid for the direct expression of heterologous genes under control of the tryptophan promoter-operator.

Figure 8:
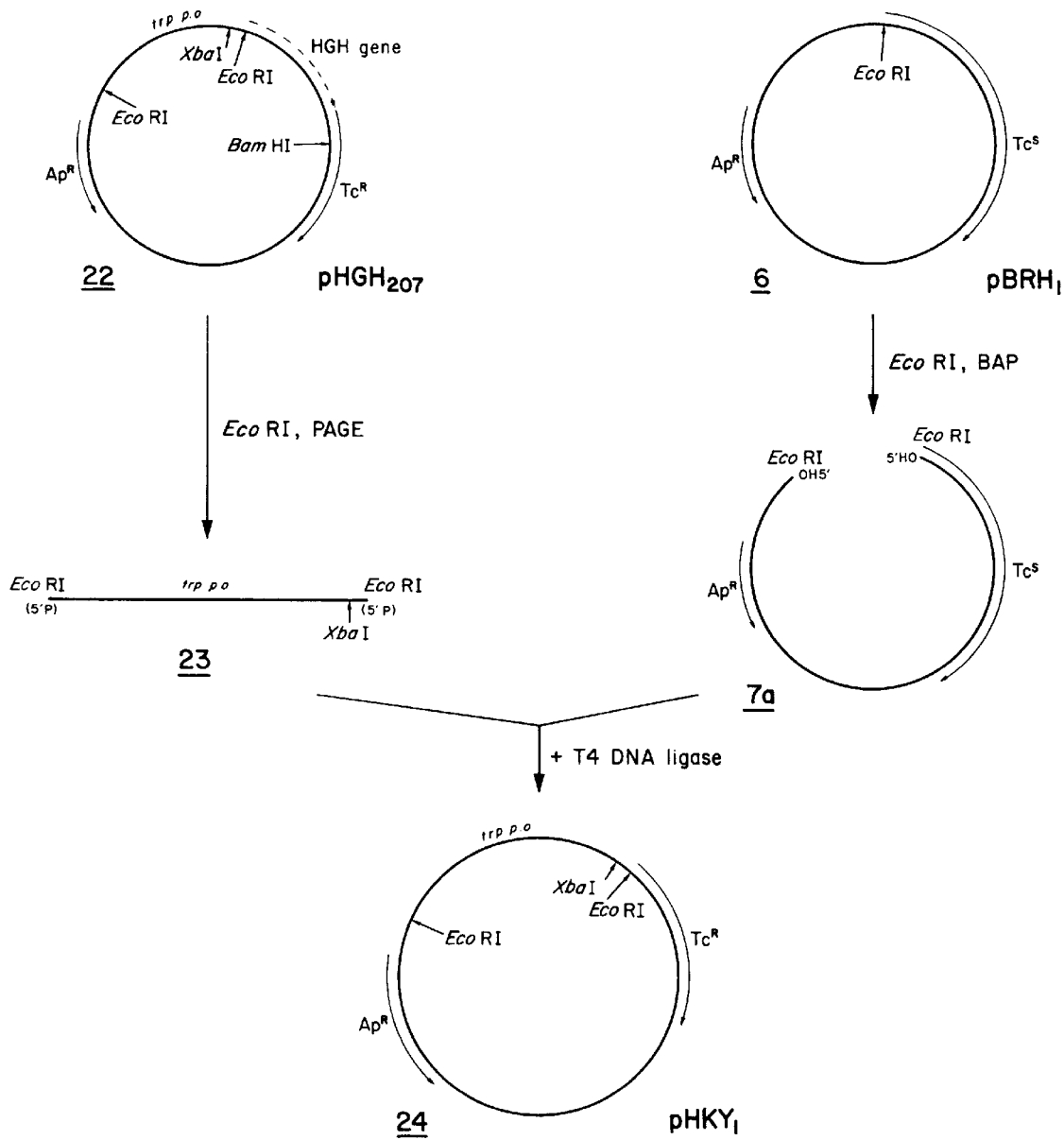
FIGS. 8, 9a, 9b and 10 illustrate in successive stages a preferred scheme for the creation of plasmids capable of expressing heterologous genes (in the illustrated case, for somatostatin) as fusions with a portion of the trp E polypeptide, from which fusions they may be later cleaved.

The plasmid pHGH 207 created in the preceding section was next used to obtain a DNA fragment containing the control elements of the tryptophan operon (with the attenuator deleted) and to create a plasmid "expression vector" suitable for the direct expression of various structural gene inserts. The strategy for creation of the general expression plasmid involved removal of the tryptophan control region from pHGH 207 by EcoRI digestion and insertion in the EcoRI-digested plasmid pBRH1 used in part I. supra. pBRH1, as previously noted, is an ampicillin resistant plasmid containing the tetracycline resistance gene but is tetracycline sensitive because of the absence of a suitable promoter-operator system. The resulting plasmid, pHKY 1, whose construction is more particularly described below and shown in FIG. 8, is both ampicillin and tetracycline resistant, contains the tryptophan promoter-operator system, lacks the tryptophan attenuator, and contains a unique XbaI site distal from the tryptophan promoter-operator. The tryptophan promoter-operator and unique XbaI site are bounded by EcoRI sites, such that the promoter-operator-XbaI-containing fragment can be removed for insertion in other structural gene-containing plasmids. Alternatively, heterologous structural genes may be inserted, either into the XbaI site or (after partial EcoRI digestion) into the EcoRI site distal from the tryptophan control region, in either case so as to come under the control of the tryptophan promoter-operator system.

Plasmid pHGH 207 was EcoRI digested and the trp promoter containing EcoRI fragment 23 recovered by PAGE followed by electroelution.

Plasmid pBRH1 was EcoRI digested and the cleaved ends treated with bacterial alkaline phosphatase ("BAP") 1 μg, in 50 mM tris pH 8 and 10 mM $MgCl_2$ for 30 min. at 6520 C.) to remove the phosphate groups on the protruding EcoRI ends. Excess bacterial alkaline phosphatase was removed by phenol extraction, chloroform extraction and ethanol precipitation. The resulting linear DNA 7a, because it lacks phosphates on the protruding ends thereof, will in ligation accept only inserts whose complementary sticky ends are phosphorylated but will not itself recircularize, permitting more facile screening for plasmids containing the inserts. The EcoRI fragment derived from pHGH 207 and the linear DNA obtained from pBRH1 were combined in the presence of $T_4$ ligase as previously described and ligated. A portion of the resulting mixture was transformed into E. coli strain 294 as previously described, plated on LB media containing 5 μg/ml of tetracycline, and 12 tetracycline resistant colonies selected. Plasmid was isolated from each colony and examined for the presence of a DNA insert by restriction endonuclease analysis employing EcoRI and XbaI. One plasmid containing the insert was designated pHKY1.

IV. Creation of a plasmid containing the tryptophan operon capable of expressing a specifically cleavable fusion protein comprising 6 amino acids of the trp leader peptide and the last third of the trp E polypeptide (designated LE') and a heterologous structural gene product.

The strategy for the creation of a LE' fusion protein expression plasmid entailed the following steps:

a. Provision of a gene fragment comprising codons for the distal region of the LE' polypeptide having Bgl II and EcoRI sticky ends respectively at the 5' and at the 3' ends of the coding strand;

b. Elimination of the codons from the distal region of the LE' gene fragment and those for the trp D gene from plasmid SOM 7 Δ2 and insertion of the fragment formed in step 1, reconstituting the LE' codon sequence immediately upstream from that for the heterologous gene for somatostatin.

Figure 9A:
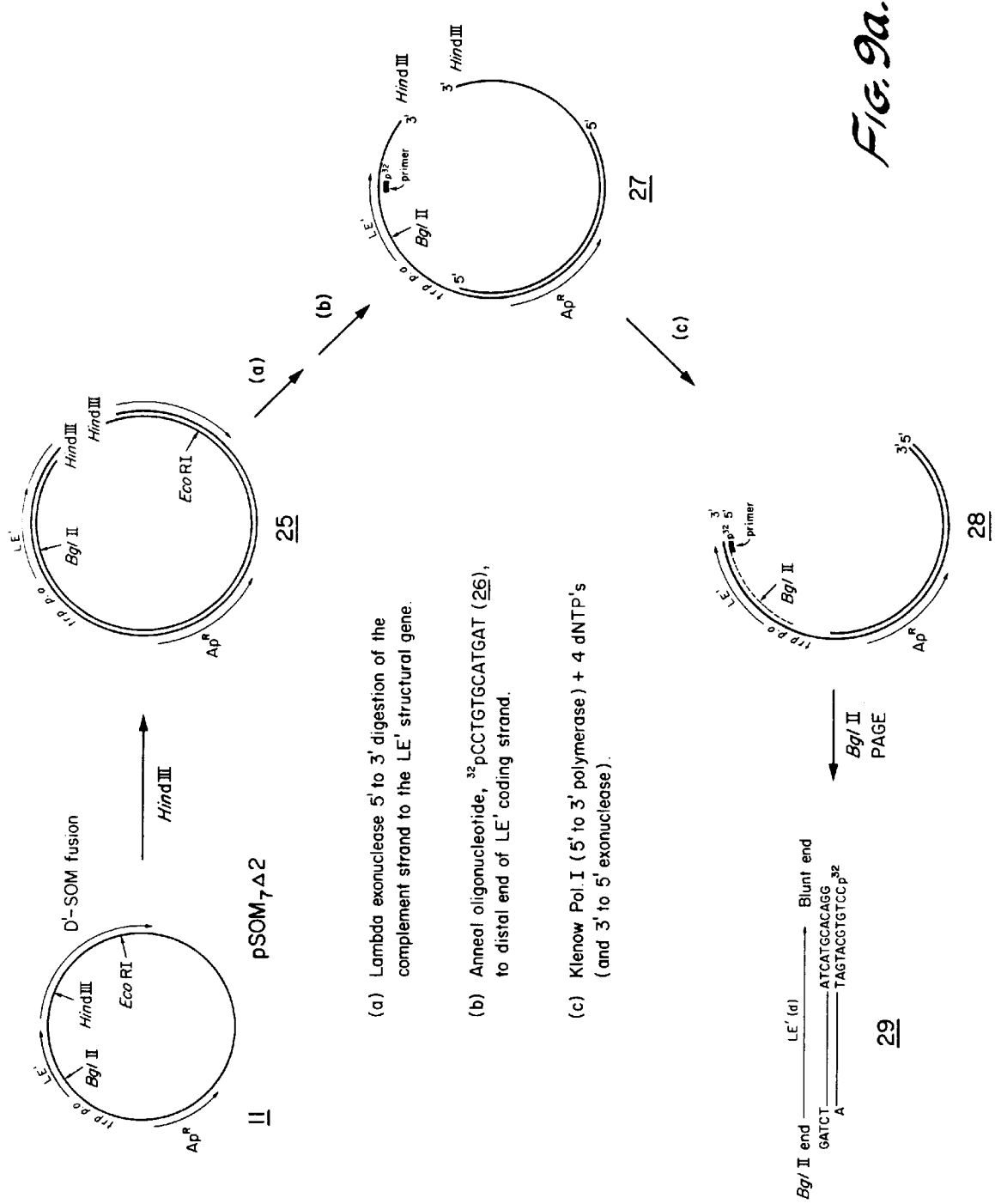

1. With reference to FIG. 9(a), plasmid pSom7 Δ2 was Hind III digested followed by digestion with lambda exonuclease (a 5' to 3'exonuclease) under conditions chosen so as to digest beyond the Bgl II restriction site within the LE' encoding region. 20 μg of Hind III-digested pSom 7 Δ2 was dissolved in buffer [20 mM glycine buffer, pH 9.6, 1 mM $MgCl_2$, 1 mM β-mercaptoethanol]. The resulting mixture was treated with 5 units of lambda exonuclease for 60 minutes at room temperature. The reaction mixture obtained was then phenol extracted, chloroform extracted and ethanol precipitated.

In order ultimately to create an EcoRI residue at the distal end of the LE' gene fragment a primer $^{32}$pCCTGTGCAT-GAT was synthesized by the improved phosphotriester method (R. Crea et al., Proc Nat'l Acad Sci USA 75, 5765 [1978]) and hybridized to the single stranded end of the LE' gene fragment resulting from lambda exonuclease digestion. The hybridization was performed as next described.

20 μg of the lambda exonuclease-treated Hind III digestion product of plasmid pSom7 Δ2 was dissolved in 20 μl $H_2O$ and combined with 6 μl of a solution containing approximately 80 picomoles of the 5'-phosphorylated oligonucleotide described above. The synthetic fragment was hybridized to the 3' end of the LE' coding sequence and the remaining single strand portion of the LE' fragment was filled in by the Klenow polymerase I procedure described above, using dATP, dTTP, dGTP and dCTP.

The reaction mixture was heated to 50° C. and let cool slowly to 1020 C., whereafter 4 μl of Klenow enzyme were added. After 15 minute room temperature incubation, followed by 30 minutes incubation at 37° C., the reaction was stopped by the addition of 5 μl of 0.25 molar EDTA. The reaction mixture was phenol extracted, chloroform extracted and ethanol precipitated. The DNA was subsequently cleaved with the restriction enzyme Bgl II. The fragments were separated by PAGE. An autoradiogram obtained from the gel revealed a $^{32}$P-labelled fragment of the expected length of approximately 470 bp, which was recovered by electroelution. As outlined, this fragment LE'(d) has a Bgl II and a blunt end coinciding with the beginning of the primer.

The plasmid pThα1 described in part I(C.) above carries a structural gene for thymosin alpha one cloned at its 5' coding strand end into an EcoRI site and at its 3' end into a BamHI site. As shown in FIG. 9, the thymosin gene contains a Bgl II site as well.

Figure 9B:
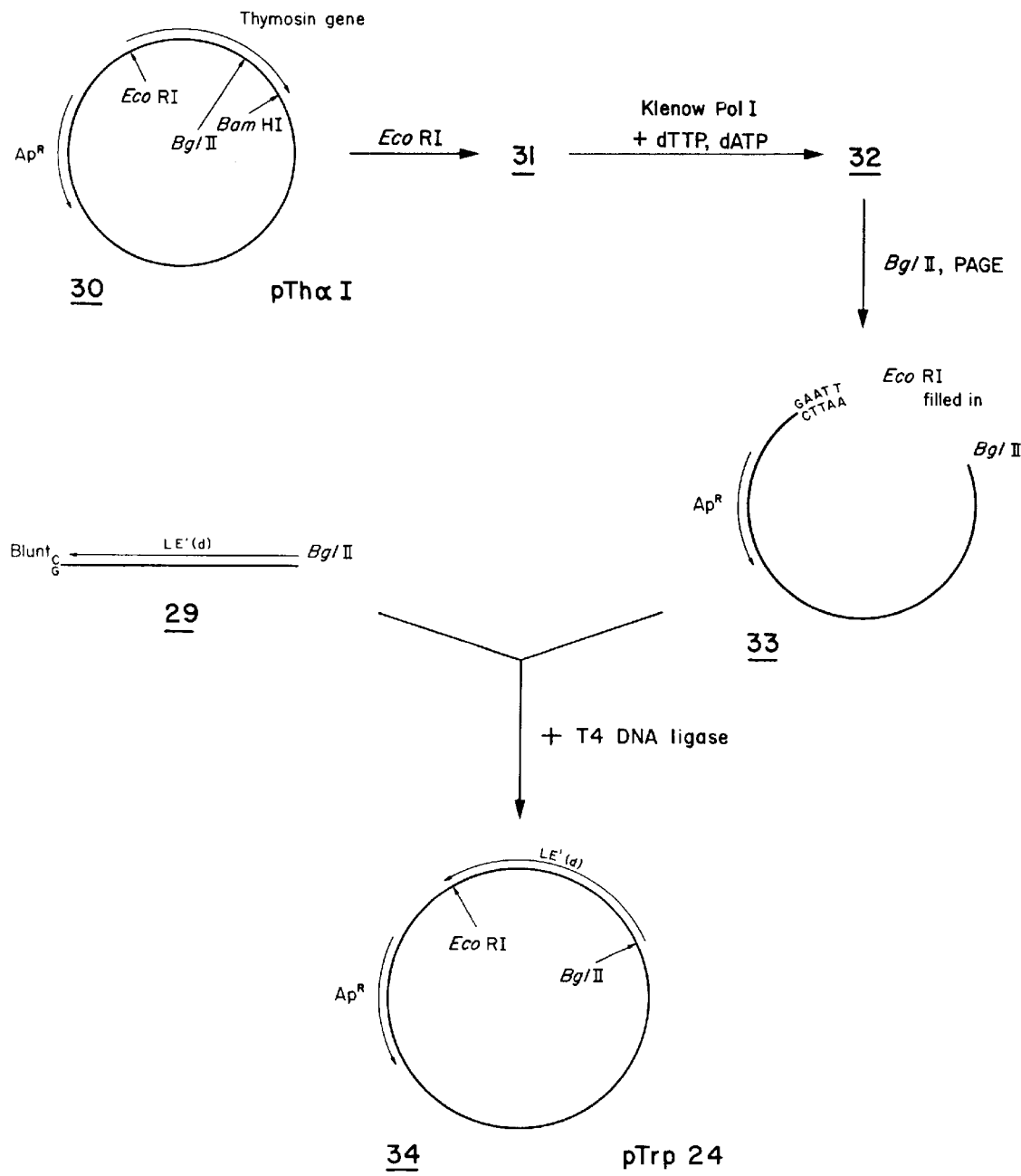

Plasmid pThα1 also contains a gene specifying ampicillin resistance. In order to create a plasmid capable of accepting the LE'(d) fragment prepared above, pThα1 was EcoRI digested followed by Klenow polymerase I reaction with dTTP and dATP to blunt the EcoRI residues. Bgl II digestion of the resulting product created a linear DNA fragment 33 containing the gene for ampicillin resistance and, at its opposite ends, a sticky Bgl II residue and a blunt end. The resulting product could be recircularized by reaction with the LE'(d) fragment containing a Bgl II sticky end and a blunt end in the presence of $T_4$ ligase to form the plasmid pTrp24 (FIG. 9b). In doing so, an EcoRI site is recreated at the position where blunt end ligation occurred.

Figure 10:
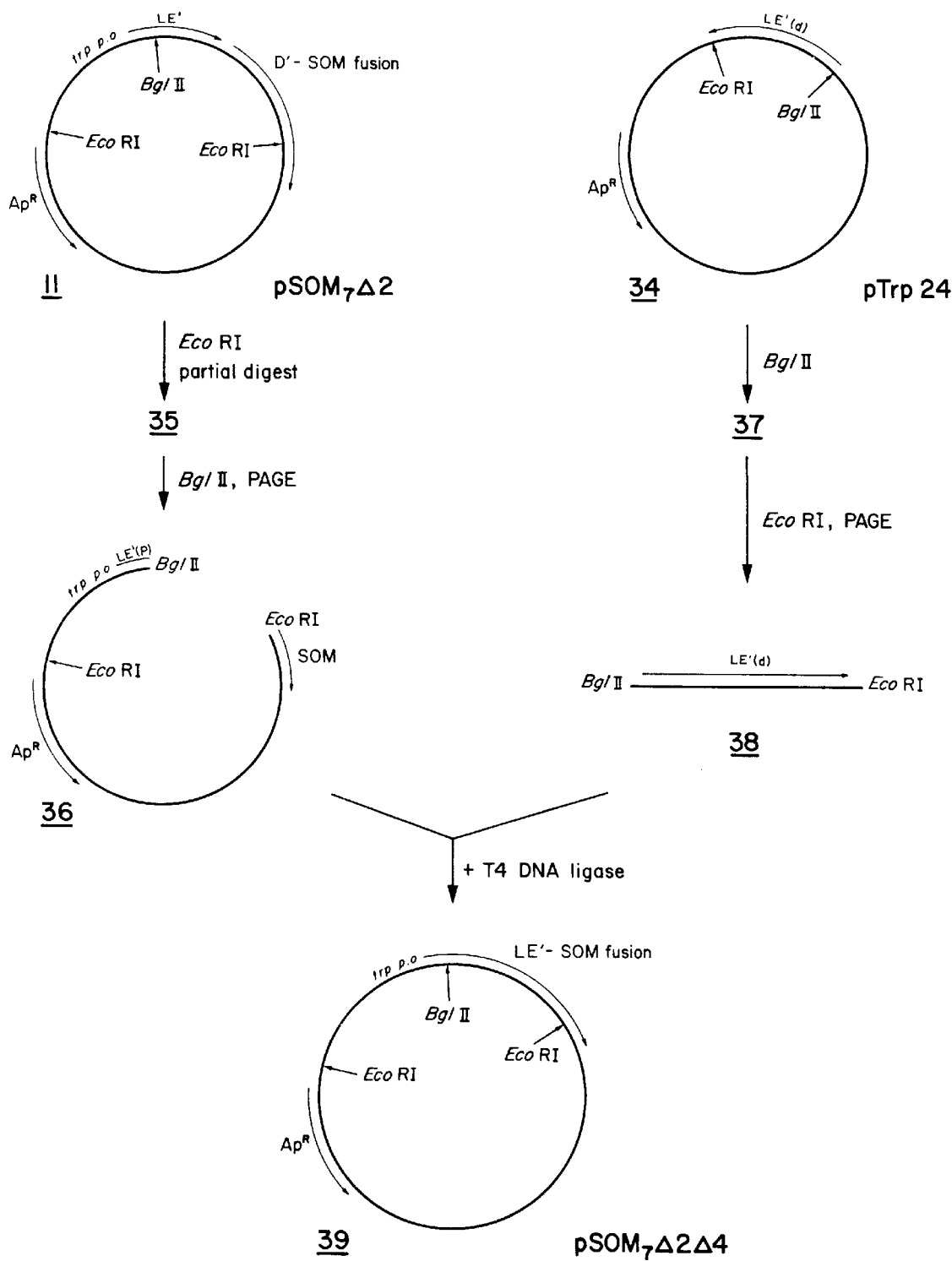

With reference to FIG. 10, successive digestion of pTrp24 with Bgl II and EcoRI, followed by PAGE and electroelution yields a fragment having codons for the LE'(d) polypeptide with a Bgl II sticky end and an EcoRI sticky end adjacent its 3' coding terminus. The LE'(d) fragment 38 can be cloned into the Bgl II site of plasmid pSom7 Δ2 to form an LE' polypeptide/somatostatin fusion protein expressed under the control of the tryptophan promoter-operator, as shown in FIG. 10. To do so requires (1) partial EcoRI digestion of pSom7 Δ2 in order to cleave the EcoRI site distal to the tryptophan promoter-operator, as shown in FIG. 10 and (2) proper choice of the primer sequence (FIG. 9) in order to properly maintain the codon reading frame, and to recreate an EcoRI cleavage site.

Thus, 16 μg plasmid pSom7 Δ2 was diluted into 200 μl of buffer containing 20 mM Tris, pH 7.5, 5 mM $MgCl_2$, 0.02 NP40 detergent, 100 mM NaCl and treated with 0.5 units EcoRI. After 15 minutes at 37° C., the reaction mixture was phenol extracted, chloroform extracted and ethanol precipitated and subsequently digested with Bgl II. The larger resulting fragment 36 isolated by the PAGE procedure followed by electroelution. This fragment contains the codons "LE'(p)" for the proximal end of the LE' polypeptide, ie, those upstream from the Bgl II site. The fragment 36 was next ligated to the fragment 33 in the presence of $T_4$ DNA ligase to form the plasmid pSom7 $\Delta2\Delta4$, which upon transformation into *E. coli* strain 294, as previously described, efficiently produced a fusion protein consisting of the fully reconstituted LE' polypeptide and somatostatin under the control of the tryptophan promoter-operator. The fusion protein, from which the somatostatin may be specifically cleaved owing to the presence of a methionine at the 5' end of the somatostatin sequence was segregated by SDS polyacrylamide gel electrophoresis as previously described. The fusion protein product is the most distinct band apparent in Lane 6 of FIG. 11, discussed in greater detail in Part VI, infra.

V. Creation of an expression system for trp LE' polypeptide fusions wherein tetracycline resistance is placed under the control of the tryptophan promoter-operator.

The strategy for creation of an expression vehicle capable of receiving a wide variety of heterologous polypeptide genes for expression as trp LE' fusion proteins under the control of the tryptophan operon entailed construction of a plasmid having the following characteristics:

1. Tetracycline resistance which would be lost in the event of the promoter-operator system controlling the genes specifying such resistance was excised.
2. Removing the promoter-operator system that controls tetracycline resistance, and recircularizing by ligation to a heterologous gene and a tryptophan promoter-operator system in proper reading phase with reference thereto, thus restoring tetracycline resistance and accordingly permitting identification of plasmids containing the heterologous gene insert.

In short, and consistent with the nature of the intended inserts, the object was to create a linear piece of DNA having a Pst residue at its 3' end and a Bgl II residue at its 5' end, bounding a gene capable of specifying tetracycline resistance when brought under the control of a promoter-operator system.

Figure 12:
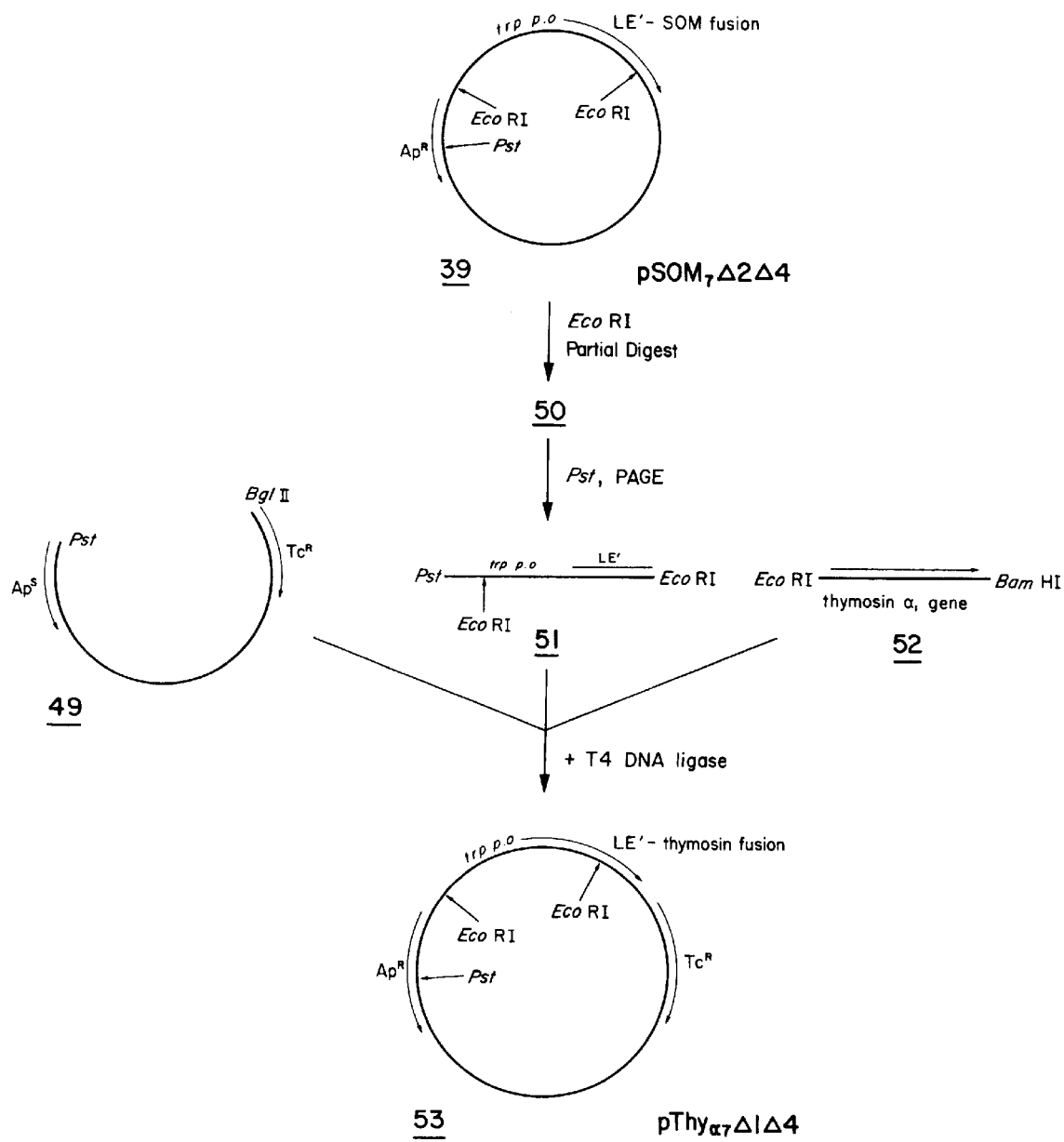
FIGS. 12 and 13 illustrate in successive stages the manner in which the plasmid created by the scheme of FIGS. 8–10 inclusive is manipulated to form a system in which other heterologous genes may be interchangeably expressed as fusions with trp E polypeptide sequences.

Thus, with reference to FIG. 12, plasmid pBR322 was Hind III digested and the protruding Hind III ends in turn digested with S1 nuclease. The S1 nuclease digestion involved treatment of 10 μg of Hind III-cleaved pBR322 in 30 μl S1 buffer (0.3 M NaCl, 1 mM $ZnCl_2$, 25 mM sodium acetate, pH 4.5) with 300 units S1 nuclease for 30 minutes at 15° C. The reaction was stopped by the additon of 1 μl of 30 X S1 nuclease stop solution (0.8 M tris base, 50 mM EDTA). The mixture was phenol extracted, chloroform extracted and ethanol precipitated, then EcoRI digested as previously described and the large fragment 46 obtained by PAGE procedure followed by electroelution. The fragment obtained has a first EcoRI sticky end and a second, blunt end whose coding strand begins with the nucleotide thymidine. As will be subsequently shown, the S1-digested Hind III residue beginning with thymidine can be joined to a Klenow polymerase I-treated Bgl II residue so as to reconstitute the Bgl II restriction site upon ligation.

Plasmid pSom7 $\Delta2$, as prepared in Part I above, was Bgl II digested and the Bgl II sticky ends resulting made double stranded with the Klenow polymerase I procedure using all four deoxynucleotide triphosphates. EcoRI cleavage of the resulting product followed by PAGE and electroelution of the small fragment 42 yielded a linear piece of DNA containing the tryptophan promoter-operator and codons of the LE' "proximal" sequence upstream from the Bgl II site ("LE'(p)"). The product had an EcoRI end and a blunt end resulting from filling in the Bgl II site. However, the Bgl II site is reconstituted by ligation of the blunt end of fragment 42 to the blunt end of fragment 46. Thus, the two fragments were ligated in the presence of $T_4$ DNA ligase to form the recircularized plasmid pHKY 10 (see FIG. 12) which was propagated by transformation into competent *E. coli* strain 294 cells. Tetracycline resistant cells bearing the recombinant plasmid pHKY 10 were grown up, plasmid DNA extracted and digested in turn with Bgl II and Pst followed by isolation by the PAGE procedure and electroelution of the large fragment, a linear piece of DNA having Pst and Bgl II sticky ends. This DNA fragment 49 contains the origin of replication and subsequently proved useful as a first component in the construction of plasmids where both the genes coding for trp LE' polypeptide fusion proteins and the tet resistance gene are controlled by the trp promoter/operator.

Figure 13:
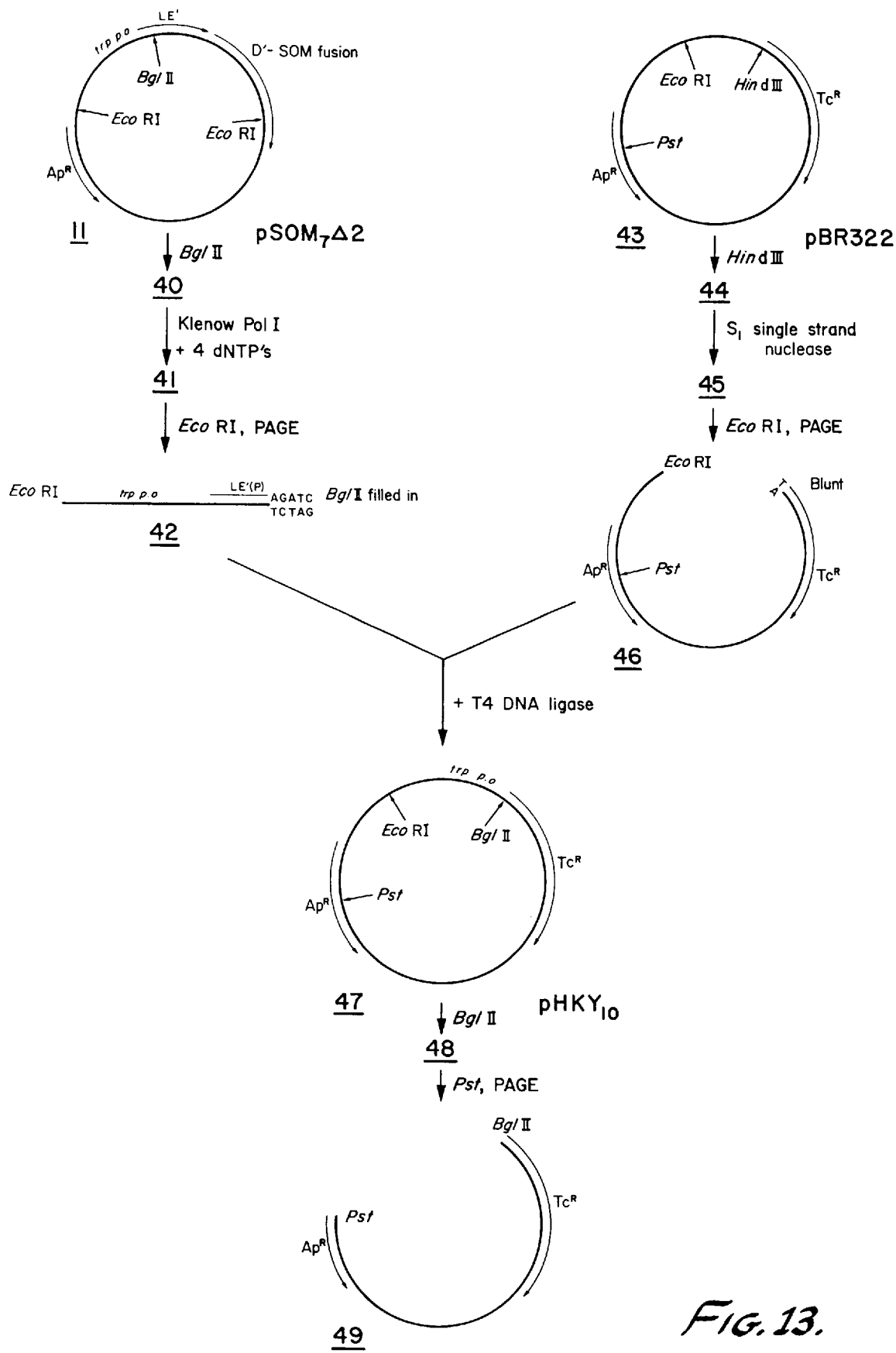

Plasmid pSom7 $\Delta2\Delta4$, as previously prepared in Part IV, could be manipulated to provide a second component for a system capable of receiving a wide variety of heterologous structural genes. With reference to FIG. 13, the plasmid was subjected to partial EcoRI digestion (see Part IV) followed by Pst digestion and fragment 51 containing the trp promoter/operator was isolated by the PAGE procedure followed by electroelution. Partial EcoRI digestion was necessary to obtain a fragment which was cleaved adjacent to the 5' end of the somatostatin gene but not cleaved at the EcoRI site present between the ampicillin resistance gene and the trp promoter operator. Ampicillin resistance lost by the Pst I cut in the $ap^R$ gene could be restored upon ligation with fragment 51.

In a first demonstration the third component, a structural gene for thymosin alpha-one was obtained by EcoRI and BamHI digestion of plasmid pThα1. The fragment, 52, was purified by PAGE and electroelution.

Figure 11:
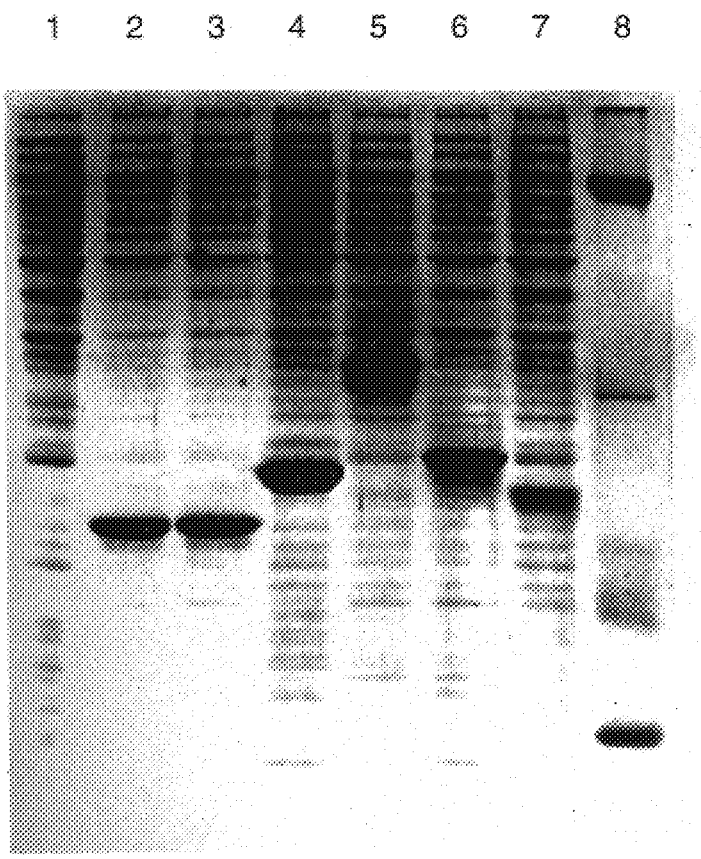
FIG. 11 is the result of polyacrylamide gel segregation of cell protein containing homologous (trp E)-heterologous fusion proteins for the production of, respectively, somatostatin, thymosin alpha 1, human proinsulin, and the A and B chains of human insulin.

The three gene fragments 49, 51 and 52 could now be ligated together in proper orientation, as depicted in FIG. 13, to form the plasmid pThα7$\Delta1\Delta4$, which could be selected by reason of the restoration of ampicillin and tetracycline resistance. The plasmid, when transformed into *E. coli* strain 294 and grown up under conditions like those described in Part I, expressed a trp LE' polypeptide fusion protein from which thymosin alpha one could be specifically cleaved by cyanogen bromide treatment. When other heterologous structural genes having EcoRI and BamHI termini were similarly ligated with the pHKY10-derived and pSOM7 $\Delta2\Delta4$-derived components, trp LE' polypeptide fusion proteins containing the polypeptides for which those heterologous genes code were likewise efficiently obtained. FIG. 11 illustrates an SDS polyacrylamide gel electrophoresis separation of total cellular protein from *E. coli* strain 294 transformants, the darkest band in each case representing the fusion protein product produced under control of the tryptophan promoter-operator system. In FIG. 11, Lane 1 is a control which segregates total cellular protein from *E. coli* 294/pBR322. Lane 2 contains the somatostatin fusion product from plasmid pSom7 $\Delta2\Delta4$ prepared in Part IV. Lane 3 is the somatostatin-containing expression product of pSom7 $\Delta1\Delta4$. Lane 4 contains the expression product of pThα7$\Delta1\Delta4$, whereas Lane 5 contains the product expressed from a plasmid obtained when the pHKY-10-derived and pSOM7 $\Delta2\Delta4$-derived fragments discussed above were ligated with an EcoRI/BamHI terminated structural gene encoding human proinsulin and prepared in part by certain of us. Lanes 6 and 7 respectively contain, as the darkest band, a trp LE' polypeptide fusion protein from which can be cleaved the B and A chain of human insulin. The insulin B and A structural genes were obtained by EcoRI and BamHI digestion of plasmids pIB1 and pIA11 respectively, whose construction is disclosed in D. V. Goeddel et al., Proc Nat'l Acad Sci USA 76, 106 [1979]. Lane 8 contains size markers, as before.

While the invention in its most preferred embodiment is described with reference to *E. coli*, other enterobacteriaceae could likewise serve as host cells for expression and as sources for trp operons, among which may be mentioned as examples *Salmonella typhimurium* and *Serratia marcesans*. Thus, the invention is not to be limited to the preferred embodiments described, but only by the lawful scope of the appended claims.

We claim:

1. A recombinant DNA vehicle suitable for the microbial expression of DNA encoding heterologous polypeptide comprising a portion of the trp operon having the promotor-operator and leader ribosome binding site, and a restriction site providing an insertion site for said DNA encoding heterologous polypeptide, wherein said restriction site is located 3' of said leader ribosome binding site as a substitute for the Taq I site of said trp promotor-operator and is selected from the group consisting of Xba I and Eco RI.

2. A vehicle according to claim 1 containing said DNA encoding heterologous polypeptide.

3. The vehicle according to claim 2 wherein said DNA encoding heterologous polypeptide encodes human growth hormone.

4. The vehicle according to claim 1 wherein said restriction site is an Xba I site.

5. The vehicle according to claim 1 wherein said restriction site is an Eco RI site.

6. The vehicle according to claims 2, 3 4 or 5 wherein said DNA encodes a cleavage site and a gene for human growth hormone.

7. A recombinant DNA vehicle suitable for the microbial expression of DNA encoding heterologous polypeptide having an initial methionine encoding translational start codon, comprising a portion of the *E. coli* trp operon having the promoter-operator, ribosome binding site, a DNA sequence encoding the *E. coli* trp leader polypeptide L and the *E. coli* trp polypeptide E with the deletion ΔLE1413, and a restriction site providing an insertion site for said DNA encoding heterologous polypeptide, wherein said restriction site is located 3' of said deletion and as a substitute for the termination codon of said trp E polypeptide and is selected from the group consisting of Xba I and Eco RI.

8. The vehicle according to claim 7 containing DNA encoding a cleavage site and a heterologous polypeptide selected from the group consisting of somatostatin, thymosin α-1, human proinsulin, human insulin A-chain, human insulin B-chain and human growth hormone in reading frame with said trp leader polypeptide L.

9. The vehicle according to claim 7 wherein said restriction site is an Xba I site.

10. A vehicle according to claim 7 wherein said restriction site is an Eco RI site.

11. A vehicle according to claims 7, 8, 9 or 10 containing DNA encoding a cleavage site and a gene for human growth hormone.

12. An *E. coli* strain transformed with the recombinant DNA vehicle according to claim 2 or 8.

* * * * *